US009370563B2

(12) United States Patent
Garzón Morales et al.

(10) Patent No.: US 9,370,563 B2
(45) Date of Patent: Jun. 21, 2016

(54) NEWCASTLE DISEASE VIRUS AND THE USE THEREOF AS A VACCINE

(75) Inventors: José Andrés Garzón Morales, Tehuacán (MX); Eduardo Lucio Decanini, Tehuacán (MX); Diana Verónica Cortes-Espinosa, Tepetitla de Lardizabal (MX); Angel Eduardo Absalon-Constantino, Tepetitla de Lardizabal (MX)

(73) Assignee: Investigación Aplicada S.A. de C.V., Tehuacán, Puebla (MX)

( * ) Notice: Subject to any disclaimer, the term of this patent is extended or adjusted under 35 U.S.C. 154(b) by 298 days.

(21) Appl. No.: 13/988,046

(22) PCT Filed: Nov. 18, 2011

(86) PCT No.: PCT/MX2011/000141
§ 371 (c)(1),
(2), (4) Date: Aug. 6, 2013

(87) PCT Pub. No.: WO2012/067483
PCT Pub. Date: May 24, 2012

(65) Prior Publication Data

US 2013/0315956 A1 Nov. 28, 2013

(30) Foreign Application Priority Data

Nov. 18, 2010 (MX) .................... MX/a/2010/012602

(51) Int. Cl.
*A61K 48/00* (2006.01)
*A61K 39/17* (2006.01)
*A61K 39/12* (2006.01)
*C07K 16/08* (2006.01)
*A61K 39/39* (2006.01)
*A61K 39/00* (2006.01)

(52) U.S. Cl.
CPC ................. *A61K 39/17* (2013.01); *A61K 39/12* (2013.01); *C07K 16/08* (2013.01); *A61K 39/39* (2013.01); *A61K 2039/5252* (2013.01); *A61K 2039/541* (2013.01); *A61K 2039/552* (2013.01); *A61K 2039/55566* (2013.01); *C07K 2317/23* (2013.01); *C12N 2760/18134* (2013.01); *C12N 2760/18163* (2013.01); *C12N 2760/18171* (2013.01)

(58) Field of Classification Search
None
See application file for complete search history.

(56) References Cited

FOREIGN PATENT DOCUMENTS

WO 2008038845 A1 4/2008

OTHER PUBLICATIONS

Int'l Search Report issued May 9, 2012 in Int'l Application No. PCT/MX2011/000141.

Absalon et al, "The complete genome of a velogenic Newcastle disease virus isolated from chickens in Mexico," retrieved from the internet at: http'//srs.ebi.ac.uk/srsbin/cgi-bin/wgetz?-e+([emblidacc-id:HM117720]>embl)|[embl-acc:HM117720]+-vn+2+-noSession> (Jun. 21, 2010).

Absalon et al, "The complete genome of a velogenic Newcastle disease virus isolated from chickens in Mexico," retrieved from http://ebi.ac.uk/uniprot/unisave/?help=0&session=/ebi/extserv/old-work/SESSION23662-1335455074-1&index=10 &view=939762679&issue_date=05-OCT-2010> (Oct. 5, 2010).

Perozo et al, "Biological and Phylogenetic Characterization of Virulent Newcastle Disease Virus Circulating in Mexico," Avian Diseases, vol. 52, pp. 472-479 (2008).

Absalon et al, "The complete genome of a velogenic Newcastle disease virus isolated from chickens in Mexico," retrieved from http://www.ebi.ac.uk/uniprot/unisave/?help=0&session=/ebi/extserv/old-work/SESSION25267-1335456253-1&index=8 &view=939762672&issue_date=05-OCT-2010 (Oct. 5, 2010).

Toyoda et al, "Identification of Amino Acids Relevant to Three Antigenic Determinants on the Fusion Protein of Newcastle Disease Virus That Are Involved in Fusion Inhibition and Neutralization," Journal of Virology, vol. 62, No. 11, pp. 4427-4430 (Nov. 1988).

Miller et al, "Comparison of Viral Shedding Following Vaccination with Inactivated and Live Newcastle Disease Vaccines Formulated with Wild-Type and Recombinant Viruses," Avian Diseases, vol. 53, pp. 39-49 (2009).

Aldous et al, "A molecular epidemiological study of avian paramyxovirus type 1 (Newcastle disease virus) isolates by phylogenetic analysis of a partial nucleotide sequence of the fusion protein gene," Avian Pathology, vol. 32, No. 3, pp. 239-257 (2003).

Mase et al, "Phylogenetic Analysis of Newcastle Disease Virus Genotypes Isolated in Japan," Journal of Clinical Microbiology, vol. 40, No. 10, pp. 3826-3830 (Oct. 2002).

Miller et al, "Antigenic differences among Newcastle disease virus strains of different genotypes used in vaccine formulation affect viral shedding after a virulent challenge," Vaccine, vol. 25, pp. 7238-7246 (2007).

Hu et al, "A vaccine candidate of attenuated genotype VII Newcastle disease virus generated by reverse genetics," Vaccine, vol. 27, pp. 904-910 (2009).

Tsai et al, "Antigenic and genotypical characterization of Newcastle disease viruses isolated in Taiwan between 1969 and 1996," Veterinary Microbiology, vol. 104, pp. 19-30 (2004).

Merino et al, "Characterization of NEwcastle disease viruses isolated from chicken, gamefowl, pigeon and quail in Mexico," Vet. Res. Commun., vol. 33, pp. 1023-1030 (2009).

Czeglédi et al, "Third genome size category of avian paramyxovirus serotype 1 (Newcastle disease virus) and Revolutionary implications," Virus Research, vol. 10, pp. 36-48 (2006).

*Primary Examiner* — Michelle S Horning
(74) *Attorney, Agent, or Firm* — Panitch Schwarze Belisario & Nadel LLP

(57) ABSTRACT

The present invention relates to a new Newcastle disease viruses of any genotype and novel fragments of the Newcastle disease virus genome encoding for the F and HN proteins constructed by reverse genetics and recombination, highly antigenic, for preparing vaccines for the prevention of the Newcastle disease by reducing viral shedding or for using as vectors with other viruses, lyophilized or in oil emulsion. Likewise, it can be used as vector in combination with other pathogenic agents.

19 Claims, No Drawings

SEQUENCE LISTING

<160> NUMBER OF SEQ ID NOS: 5

<210> SEQ ID NO 1
<211> LENGTH: 3650
<212> TYPE: DNA
<213> ORGANISM: Newcastle disease virus

<400> SEQUENCE: 1
ggtagaagat tctggatccc ggttggcgcc ctccaggtgc aagatgggct ccagaccttc 60
taccaagaac ccagcaccta tgatgctgac tatccgggtt gcgctggtac tgagttgcat 120
ctgtccggca aactccattg atggcaggcc tcttgcagct gcaggaattg tggttacagg 180
agacaaagcc gtcaacatat acacctcatc ccagacagga tcaatcatag ttaagctcct 240
cccgaatctg cccaaggata aggaggcatg tgcgaaagcc cccttggatg catacaacag 300
gacattgacc actttgctca cccccttgg tgactctatc cgtaggatac aagagtctgt 360
gactacatct ggaggggga gacaggggcg ccttataggc gccattattg gcggtgtggc 420
tcttggggtt gcaactgccg cacaaataac agcggccgcg gctctgatac aagccaacca 480
gaacgctgcc aacatcctcc ggcttaagga gagcattgct gcaaccaatg aagctgtaca 540
tgaggtcact gacggattat cacaactagc ggtggcggtt gggaagatgc agcagtttgt 600
taatgaccag tttaataata cggcgcgaga attggactgc ataaaaatta cacaacaggt 660
tggtgtcgaa ctcaatttgt acctaacaga gttgactaca gtgttcgggc cacaaatcac 720
ctcccctgct ttaactcagc tgaccatcca ggcactttat aatttagctg gtggcaatat 780
ggattacttg ttgactaagt taggtgtagg gaacaatcaa ctcagctcgt taattggtag 840
tggcttgatc accggcaacc ctatactata tgactcacag acccaactct tgggcataca 900
ggtaaattta ccctcagtcg ggaacctaaa taatatgcgt gccacctact tggagacctt 960

-continued atccgtaagc acaaccaaag ggttcgcctc agcccttgtc ccgaaagttg tgacgcaagt 1020
cggttctgtg atagaagaac ttgatacctc atattgtata gaatccgatc tggatttata 1080
ttgcacaagg gtagtgacat tccccatgtc tcctggtatt tattcctgtc tgagcggcaa 1140
tacgtcagct tgtatgtatt caaagactga aggtgcactc actacaccat acatggccct 1200
caaaggctca gttattgcca attgcaagat gattacatgc agatgtgcag atcccccagg 1260
tatcatatcg caaaattacg gggaagctgt gtccctaata gataaacact catgcaatgt 1320
cttatcccta gacgggataa ccctgaggct cagtggggaa tttgatgcga cttatcaaaa 1380
gaacatctca atactagact ctcaagtcat cgtgacaggc aatctcgata tatcaactga 1440
gcttgggaat gtcaacaact cgataagcag tgccctggac aaattagcgg aaagcaacag 1500
caggctaaac aaagtcaatg tcaacctaac cagcacatct gctctcatta cttatattgt 1560
tttagctgtc atatctcttg ctttcggtgt aattagcctg gttctagcgt gctacctgat 1620
gtataaacaa aaagcacaac aaaagacctt actatggctt gggaacaata ccctcgatca 1680
gatgagagcc actacaagaa catgaataca gatgagagac gaatgtatcc ccagtagcaa 1740
ttcgtgcgtc aattctgata gcctgccaat tgggagaatt aagaaaaaac tactggatat 1800
aagtgaccaa agagcaatac acgggtagaa cggtcggaga agccacccct tagtcaggaa 1860
ccaggcttca caacatccgt tctaccgcat taccaatagc agacttcagt catggatcgt 1920
gtagttagca gagttgtact agagaacgaa gaaagagaag caaagaacac atggcgcttg 1980
gttttccgga tcgcagtctt atctctagta gtaatgactt tagctatctc tgtagccgcc 2040
ctggtataca gcatgggggc tagcacaccg agcgaccttg caggcatatc gacggtgatc 2100
tctaaggcag aggatagggt tacatcttta ctcagttcaa atcaagatgt ggtagatagg 2160
gtatataaac aggtggccct tgagtccccg ctggcgttgc taaatactga atctataatt 2220
atgaatgcaa taacttctct ctcttatcaa attaatgggg ctgcaaataa tagtgggtgt 2280
ggggcacctg ttcatgaccc agattatatt ggggggggtag gcaaagaact catagtagat 2340
gacacaagtg atgtcacatc attctatcct tcagcatacc aagaacacct gaattttatc 2400
ccggcgccta ctacaggatc aggctgcact cggataccct cattcgacat gagcactacc 2460
cactattgtt atactcacaa tgtgatatta tctggttgca gagatcactc acactcacat 2520
cagtatttag cgctaggtgt acttcggaca tccgcaacag ggagggtatt cttttctact 2580
ctgcgttcca tcaatttaga tgacacccaa aatcggaagt cttgcagtgt gagtgcgact 2640
cctttaggtt gtgatatgct gtgctctaaa gtcatagaga ctgaggagga ggattataag 2700
tcaattaccc ccacatcaat ggtgcatgga aggttagggt ttgacggtca gtaccatgag 2760
aaggacttag acgtcacagt cttatttaag gattgggttg caaattaccc gggagtggga 2820
ggagggtctc ttattgacga ccgtgtatgg ttcccagttt atggagggct aaaacccaat 2880
tcgcctagcg acactgcaca agaagggaga tatgtaatat acaagcgcta taataacaca 2940
tgccccgatg gacaagatta ccaagttcgg atggctaagt cttcgtataa gcctggacgg 3000
tttggtagaa agcgcgtaca gcaagccatc ttatctatca aagtatcaac atctttgggc 3060
gaggacccgg tgctgactgt accgccaaat acagttacac tcatgggggc cgaaggcaga 3120
gtcctcacag tagggacatc tcatttcttg taccaacgag ggtcttcata cttctctccc 3180
gccttattat accctatgac agtacacaac aaaacagcta ctcttcatag tccttatata 3240
tttaatgctt tcactcggcc aggtagtgtc ccttgccagg catcagcaag gtgccctaac 3300
tcatgtatca ctggagtcta tactgatccg tatcctttag tcttccatag gaatcacacc 3360

-continued ttgcgagggg tgttcgggac aatgcttgat aatgaacaag caaggttcaa ccccgtatct 3420
gcagtatttg attacacatc tcgcagtcgc ataacccggg taagttcaag cagcaccaag 3480
gcagcataca cgacatcgac atgttttaaa gttgtcaaga ccaataaagt ttattgcctt 3540
agcattgcag aaatatccaa caccctattt ggggaattca ggattgtccc tttactagtt 3600
gagatcctca aagatgacgg ggttagagaa gccaggtctg gctagttgag 3650

<210> SEQ ID NO 2
<211> LENGTH: 15192
<212> TYPE: DNA
<213> ORGANISM: Newcastle disease virus

<400> SEQUENCE: 2
accaaacaga gaatcggtga gatacgataa aaggcgaaga agcaatcgaa atcgtacggg 60
tagaaggtgt gaacctcgag tgcgaggccg aaactcaaac tcgaggaagc cttctaccga 120
catgtcgtcc gtatttgacg aatacgagca actcctcgct gctcagactc gccctaatgg 180
agcccacgga ggaggagaga aagggagcac tttgaaagtt gaggtcccag tatttactct 240
taatagtgac gatccagaag atagatggaa tttttcagta ttctgtcttc ggattgccgt 300
tagtgaggat gccaacaagc cactcaggca aggtgctctt atatccctct tatgctccca 360
ttctcaagtg atgaggaacc atgttgccct tgcagggaaa cagaatgagg ccacactggc 420
tattcttgag attgatgggt ttgccaacag cacaccccag ttcaacaaca ggagtggagt 480
gtccgaggag agagcacaga gattcatggt gatagccggg tctctccctc gggcatgcag 540
caacggtact ccgttcgtca cagccggggt tgaagatgat gcaccagaag acatcactga 600
cactctggaa aggatcctat ctatccaggc tcaggtatgg gtcacagtag cgaaggctat 660
gactgcatat gagacagcag atgagtcgga aacaagaaga atcaataagt atatgcagca 720
aggcagagtc caaaagaaat acatcctcca ccctgtatgc aggagtgcaa ttcaactcac 780
aatcaggcat tctttggcag ttcgcatttt cttagttagc gagcttaaga gaggccgcaa 840
tacggcaggt gggagctcca catattacaa cttagtaggg gatgtagact catacatcag 900
gaacactggg cttactgcat tcttcttgac actcaaatat ggaattaata ccaagacgtc 960
agctcttgca ctcagcagcc tcacaggcga tatccaaaaa atgaagcagc tcatgcgttt 1020
atatcggatg aagggagaaa atgcaccgta catgacattg ctaggcgaca gtgaccagat 1080
gagctttgca ccagctgagt atgcacaact ttattctttt gccatgggca tggcatcagt 1140
cttagataaa ggaactggca aataccaatt cgccagagac tttatgagca catcattctg 1200
gagacttggg gtagaatatg ctcaggctca ggggagtagc atcaatgagg acatggctgc 1260
tgagctaaaa ctaaccccgg cagcaaggag aggcctggca gctgctgccc aacgagtgtc 1320
cgaggaaatt ggcagcatgg atgttcctac tcaacaggcc ggggtcctca ctggactcag 1380
tgacggaggc ccccaagccc cacagggcgg atcgaacaag tcgaaagggc aaccggatgc 1440
cggggacgga gagacccaat tcttggattt gatgagagcg gtggcaaata gcatgcgaga 1500
agcacaaaat tccgcaccga gcaccaccca tccagagcct cccccaactc ctgggccatc 1560
cccagacaac gacaccgact gggggtactg attgacaaca cccagcctgc ccccacaggg 1620
tcgccccgaa tcctccgccc aaacccctct ctcactcccc gacccacagc ctcgcatggc 1680
cgagccaaca aaagtacccc cccatcctct ctcccacccc cagctgcaca accccacccg 1740
cccaaaacaa cacaggcgca acttgaccca ccaacagtcc gtgcagagcc aaagatatta 1800

-continued

```
gaaaaaagta cgggtagaag agagacgccc agagaccagg acaagtcacc aaggtctctg   1860
ttctcccttc tacctagtgg actagggcga agatggccac ctttacagat gcagagatag   1920
acgacatact tgagaccagt ggaaccgtca ttgacagcat aatcacggcc cagggcaaat   1980
caacagagaa cttcggaagg agcgcaatac cgcaaggtaa gacaaaagca ccgagcacag   2040
catgggagaa acatggggac atccaaccat ccgctagtca ggacaccctt gaccaacagg   2100
atggatcaga caaacagccg tccacaccca agcaggcgac ctcacacaac agcccgccag   2160
ccacacccac cgaaccgccc cccactcagg ccgcgggcga ggctggcgac gcgcagctca   2220
agaccggagc aagcaaccct cttttgtcca tgctcgacaa gctgagcaat aaatcgtcta   2280
atactaaaaa gggcccatgg tcaagtcctc aaggaggaca tcaccaacct ctggccaaac   2340
aacatgggaa tcagccgagc cacgggaacc accaggaaaa atctcagcac caggccaagg   2400
ccgcccctgg aagccggggc acagacgtga acacagcata tcatggacaa cagaaggagt   2460
cacaactatc agctggtgca atccctcatg cgctccagtc agggcagagc caagacaata   2520
ctcctgtatc tgtggatcat gtccagccac ctgtcgactt tgtgcaggca atgatgtcta   2580
cgatggaggc gttattgcag aaggtaaata aagttgacta tcagctagat ctagtcttga   2640
agcagacatc ctccatccct atgatgcgaa ctgaaatcca acagctgaaa acatctgttg   2700
cggtcatgga agccaattta ggcatgatga aaattctgga ccctggttgt gctaacattt   2760
catccttaag cgatctacgg gcagtcgctc gatcccaccc agttttagtt tcaggccccg   2820
gagatccgtc tccttatgtg acacaaggag gtgaattgac actcaataaa ctctcgcaac   2880
cagtacaata cccttccgag ttaattaaat ccgccgcggc aagcgggcct gacatgggag   2940
tggagaaaga cactgtccgt gcattgatca cttcacgccc gatgcatccg agctcctcag   3000
ctaagctcct gagtaagctg gatgcagcca ggtcgattga ggagatcagg aaaatcaaac   3060
gccttgcgct gaatggttga tcaccatcac aacctacaac aggttcctgc ctctttagtg   3120
tcacaaggga tccgtcctag gcccctcccc acaagtctac gctccagcac tccaagtaac   3180
aaccctctct cacctcctct accccattga atgatcgcgc aactacagtt aatctaacag   3240
cattgaagat taagaaaaaa tacgggtaga atcaaagtgc cccgactgtg ccaaaatgga   3300
ctcatccagg acaatcggac tgtactttga ttctgccctt ccttccagca gcctgcttgg   3360
ttttccgatt gtccttcaaa acacaggagg tgggaagaag caaatccccc caccatatag   3420
gatccaacgg gttggattgt gggcaggcag caaagaaggt ttggtttttt tccccacata   3480
cgggttcatt tttcaaattg gaaaagaaga agtcaccgtt ggcacgatta acgataaacc   3540
caggcaagag ttaatttttt ttgcaatggt ttgccttggg ggggtccctt atggcgggga   3600
attcgttgag ccggggaggg cctgcctcgc tatgggggta acgtgcaaga agggggcaaa   3660
ccattatgag agaatagttt tttcgatagg gcaggccccc cggggggtgg aaaactgtaa   3720
ggttgtggca aataggtact catcagtgaa agcagttaag ccagtaaaag cccccgagaa   3780
gattcccggg aacggaaatt tagagtataa ggtgaacttt gtctctttga ctgtggtgcc   3840
gaggaaggat gtctacagga tcccaaccgc agcattgaaa gtatctggct cgagcctgta   3900
taatcttgcg ctcaatgtca ctattgatgt ggaggtggat ccgaagagcc cattagtcaa   3960
atccctttcc aagtccgata gtggatacta tgctaacctt tttttacata tcgggcttat   4020
gtccactgta gataaaaagg gaaagaaagt gacatttgac aagctggaaa ggaagataag   4080
aagactcaat ctatctgttg ggctcagtga tgtgctcgga ccttccgtgc ttgtgaaggc   4140
gagaggtgca cggactaagc tgttggcacc tttcttctct agcagtggga cagcctgcta   4200
```

-continued

```
ccctatagca aatgcttctc cccaggttgc taagatactc tggagtcaga ctgcgcacct   4260
gcgaagtgta aaggtcatca ttcaagcagg cacccaacgt gctgtcgcag tgaccgctga   4320
tcatgaggtt acctctacta agatagagaa gaggcatact attgctaaat acaacccttt   4380
taagaaatag gttgtattcc tgatactatg gtctgcccgc tttcttgaat catcatgaca   4440
caaaaaacta atctgtcttg attatttaca gttagtttac ctgtctatca agttagaaaa   4500
aacacgggta gaagattctg gatcccggtt ggcgccctcc aggtgcaaga tgggctccag   4560
accttctacc aagaacccag cacctatgat gctgactatc cgggttgcgc tggtactgag   4620
ttgcatctgt ccggcaaact ccattgatgg caggcctctt gcagctgcag gaattgtggt   4680
tacaggagac aaagccgtca acatatacac ctcatcccag acaggatcaa tcatagttaa   4740
gctcctcccg aatctgccca aggataagga ggcatgtgcg aaagccccct tggatgcata   4800
caacaggaca ttgaccactt tgctcacccc ccttggtgac tctatccgta ggatacaaga   4860
gtctgtgact acatctggag gggggagaca ggggcgcctt ataggcgcca ttattggcgg   4920
tgtggctctt ggggttgcaa ctgccgcaca aataacagcg gccgcggctc tgatacaagc   4980
caaccagaac gctgccaaca tcctccggct taaggagagc attgctgcaa ccaatgaagc   5040
tgtacatgag gtcactgacg gattatcaca actagcggtg gcggttggga agatgcagca   5100
gtttgttaat gaccagttta ataatacggc gcgagaattg gactgcataa aaattacaca   5160
acaggttggt gtcgaactca atttgtacct aacagagttg actacagtgt tcgggccaca   5220
aatcacctcc cctgctttaa ctcagctgac catccaggca ctttataatt tagctggtgg   5280
caatatggat tacttgttga ctaagttagg tgtagggaac aatcaactca gctcgttaat   5340
tggtagtggc ttgatcaccg gcaaccctat actatatgac tcacagaccc aactcttggg   5400
catacaggta aatttaccct cagtcgggaa cctaaataat atgcgtgcca cctacttgga   5460
gaccttatcc gtaagcacaa ccaaagggtt cgcctcagcc cttgtcccga aagttgtgac   5520
gcaagtcggt tctgtgatag aagaacttga tacctcatat tgtatagaat ccgatctgga   5580
tttatattgc acaagggtag tgacattccc catgtctcct ggtatttatt cctgtctgag   5640
cggcaatacg tcagcttgta tgtattcaaa gactgaaggt gcactcacta caccatacat   5700
ggccctcaaa ggctcagtta ttgccaattg caagatgatt acatgcagat gtgcagatcc   5760
cccaggtatc atatcgcaaa attacgggga agctgtgtcc ctaatagata aacactcatg   5820
caatgtctta tccctagacg ggataaccct gaggctcagt ggggaatttg atgcgactta   5880
tcaaaagaac atctcaatac tagactctca agtcatcgtg acaggcaatc tcgatatatc   5940
aactgagctt gggaatgtca acaactcgat aagcagtgcc ctggacaaat tagcggaaag   6000
caacagcagg ctaaacaaag tcaatgtcaa cctaaccagc acatctgctc tcattactta   6060
tattgtttta gctgtcatat ctcttgcttt cggtgtaatt agcctggttc tagcgtgcta   6120
cctgatgtat aaacaaaaag cacaacaaaa gaccttacta tggcttggga acaataccct   6180
cgatcagatg agagccacta caagaacatg aatacagatg agagacgaat gtatccccag   6240
tagcaattcg tgcgtcaatt ctgatagcct gccaattggg agaattaaga aaaaactact   6300
ggatataagt gaccaaagag caatacacgg gtagaacggt cggagaagcc accccttagt   6360
caggaaccag gcttcacaac atccgttcta ccgcattacc aatagcagac ttcagtcatg   6420
gatcgtgtag ttagcagagt tgtactagag aacgaagaaa gagaagcaaa gaacacatgg   6480
cgcttggttt tccggatcgc agtcttatct ctagtagtaa tgactttagc tatctctgta   6540
```

-continued

```
gccgccctgg tatacagcat gggggctagc acaccgagcg accttgcagg catatcgacg   6600
gtgatctcta aggcagagga tagggttaca tctttactca gttcaaatca agatgtggta   6660
gatagggtat ataaacaggt ggcccttgag tccccgctgg cgttgctaaa tactgaatct   6720
ataattatga atgcaataac ttctctctct tatcaaatta atggggctgc aaataatagt   6780
gggtgtgggg cacctgttca tgacccagat tatattgggg gggtaggcaa agaactcata   6840
gtagatgaca caagtgatgt cacatcattc tatccttcag cataccaaga acacctgaat   6900
tttatcccgg cgcctactac aggatcaggc tgcactcgga taccctcatt cgacatgagc   6960
actacccact attgttatac tcacaatgtg atattatctg gttgcagaga tcactcacac   7020
tcacatcagt atttagcgct aggtgtactt cggacatccg caacagggag ggtattcttt   7080
tctactctgc gttccatcaa tttagatgac acccaaaatc ggaagtcttg cagtgtgagt   7140
gcgactcctt taggttgtga tatgctgtgc tctaaagtca tagagactga ggaggaggat   7200
tataagtcaa ttacccccac atcaatggtg catggaaggt tagggtttga cggtcagtac   7260
catgagaagg acttagacgt cacagtctta tttaaggatt gggttgcaaa ttacccggga   7320
gtgggaggag ggtctcttat tgacgaccgt gtatggttcc cagtttatgg agggctaaaa   7380
cccaattcgc ctagcgacac tgcacaagaa gggagatatg taatatacaa gcgctataat   7440
aacacatgcc ccgatggaca agattaccaa gttcggatgg ctaagtcttc gtataagcct   7500
ggacggtttg gtagaaagcg cgtacagcaa gccatcttat ctatcaaagt atcaacatct   7560
ttgggcgagg acccggtgct gactgtaccg ccaaatacag ttacactcat gggggccgaa   7620
ggcagagtcc tcacagtagg gacatctcat ttcttgtacc aacgagggtc ttcatacttc   7680
tctcccgcct tattataccc tatgacagta cacaacaaaa cagctactct tcatagtcct   7740
tatatattta atgctttcac tcggccaggt agtgtccctt gccaggcatc agcaaggtgc   7800
cctaactcat gtatcactgg agtctatact gatccgtatc ctttagtctt ccataggaat   7860
cacaccttgc gaggggtgtt cgggacaatg cttgataatg aacaagcaag gttcaacccc   7920
gtatctgcag tatttgatta cacatctcgc agtcgcataa cccgggtaag ttcaagcagc   7980
accaaggcag catacacgac atcgacatgt tttaaagttg tcaagaccaa taaagtttat   8040
tgccttagca ttgcagaaat atccaacacc ctatttgggg aattcaggat tgtcccttta   8100
ctggtcgaga tcctcaagga tgatagggtt taagaggcta agttcagcca gccgggtcaa   8160
ccacaagagg gatgggaaga tgacgttgta ttacctatct tctgcaatgc caaggatcaa   8220
gcggaatact aatacgagcc cgaatcttat gctatcgagc agccataatc ggataatgct   8280
gacatgatca gtttgaatct tgtcaatagt cactctgttt agaaaaaata tgaaaggtgg   8340
tgggatataa gaaaaaacaa cttacagaag atggcacggg taggacatgg cgggctccgg   8400
tcccgaaagg gcagagcacc agattatcct accagagtca catctttcct ccccattagt   8460
caaacacaaa ttgctctatt actggaaatt aactgggcta ccgcttcctg acgaatgtga   8520
ttttgaccat ctcattatca gcaggcaatg gaagaaaatc cttgagtcag ccactcctga   8580
cactgagaga atgataaaac tcgggcgggc agtgcaccag actctcaacc acaattctaa   8640
gataaccgga gtgctccatc ctaggtgttt agaagaattg gctagtattg aggtccctga   8700
ttcaactaac aagtttcgga agatcgaaaa gaagatccag attcacaaca caagatatgg   8760
agaaaagttc acgaggctgt gcacgcacgt tgaaaagaaa ttgctaggat catcctggtc   8820
tagcaatgtc ccacgatcag aggaattcaa cagcatccgt atggatccag cattctggtt   8880
tcactcaaaa tggtccagag ccaagtttgc ctggctccat ataaaacaag tccaaagaca   8940
```

-continued

```
tctgattgta gcagcaagaa caaggtccgc agtcaacaaa ctagtgacac tgactcataa   9000
gataggccaa gtctttgtta ctcctgagct tgtcattgtg acacatacag atgagaacaa   9060
gttcacatgc ctcacccagg aacttgtatt gatgtatgca gatatgatgg agggcaggga   9120
tatggtcaac ataatatcta ccacggcgac acatctcaga agcctatcag agaaaattga   9180
tgatgttctg cggttagtgg atgctctagc aaaagatttg ggcaaccggg tctatgatgt   9240
tgtatcactg atggagggat tcgcatacgg tgccgttcag ctgctcgagc cgtcaggtac   9300
atttgcagga gatttttttg cattcaacct acaggagctc aaagatactc taatcgaact   9360
cctcccaaat gatatagcag aatcagtgac tcacgcaatc gccaccatct tctccggctt   9420
agaacagaat caagcagctg agatgttgtg tttgctgcgt ttgtgggggc acccactgct   9480
tgagtcccgt attgcagcaa aagcagtcag gagccagatg tgcgcaccaa agatgctaga   9540
cttcgatatg atcctccagg tattatcttt ctttaaggga acaatcatca atggatacag   9600
aaagaagaac tcgggtgtgt ggccacgtgt caagatagat acaatatacg ggaatgtcat   9660
tagacagctg cacgctgatt cagcagagat ctcacatgat gtcatgttga gggagtacaa   9720
gagtctatct gcacttgagt tcgagccatg tatagattat gaccctgtca ccaacctaag   9780
catgttctta aaagacaagg caatcgcaca tccaaaagat aactggctcg cctcattcag   9840
gcgaaacctt ctctctgagg accagaagaa acatgtaaag gaggcgacct caactaatcg   9900
cctcttgata gagttcttgg aatcaaatga ttttgatcca tataaggaga tggaatactt   9960
gacaaccctt gagtacctaa gagatgacaa tgtagctgta tcatactcac tcaaagagaa  10020
ggaagtgaaa gttaatgggc ggattttcgc taaattaacc aagaaattaa ggaactgtca  10080
ggtaatggca gaaggaattc tagctgacca aattgcacct tttttccagg ggaatggggt  10140
cattcaggat agcatatcct tgactaagag tatgttagca atgagccaac tatcttttaa  10200
cagcaataag aaacgtatca ctgactgcaa agaaagggtt tcctcaaacc gcaatcatga  10260
tccaaaaaac aagaatcgcc gaagagttgc cacttttatc acgactgacc tgcagaagta  10320
ctgtcttaac tggagatatc agacaatcaa gctatttgcc cacgccatca accagctgat  10380
gggcctacct cacttctttg agtggattca tcttagacta atggacacta cgatgtttgt  10440
aggagaccct ttcaatcctc cgagtgaccc gaccgactgt gatctctcaa gagtcccaaa  10500
tgaagacata tatattgtca gtgctagggg gggcattgag gggttatgcc agaagctatg  10560
gacaatgatc tcgattgctg caatccaact tgctgcagca agatcgcatt gtagagttgc  10620
ctgcatggta caaggtgaca atcaagtaat agctgtaacg agagaggtaa ggtcagatga  10680
ctcctcggat atggtgttga cacagttgca ccaggccagt gataatttct tcaaagagct  10740
ggttcatgtc aatcatctga ttggccataa cctaaaagat cgtgaaacca tcaggtcaga  10800
cacattcttc atatatagca aacgaatatt caaagatgga gcaatactca gtcaggtcct  10860
taagaactca tctaaattag tgctgatatc aggtgacctt agtgaaaaca ctgtaatgtc  10920
ctgtgccaac attgcatcca ctatagcacg gctgtgtgag aacgggcttc ctaaggactt  10980
ctgttattat ttaaactacc taatgagttg cgtacaaaca tatttcgatt ctgagttttc  11040
cattactcac agctcgcagc cagattccaa ccagtcctgg attgaggaca tctctttcgt  11100
acattcgtac gtcttaaccc ctgcccagtt ggggggactg agtaatcttc aatactcaag  11160
gctctacaca aggaacatcg gtgacccggg gaccactgcc tttgcagagg tcaagagatt  11220
agaagcagtg gggttgctga gtcctagcat tatgactaac atcttaacaa ggccacctgg  11280
```

-continued

```
caatggagat tgggccagtc tttgcaacga tccatactcc tttaattttg agactgtcgc  11340
aagcccaaat attgtcctta agaaacatac acagaaagtc ttattcgaaa cttgttcaaa  11400
cccctlatta tccggagtac atacagagga taatgaggca gaagagaagg cattggctga  11460
attcttactc aatcaagaag tggttcatcc acgtgtcgcg catgctatca tggaagcaag  11520
ctctgtaggt aggagaaagc aaatccaagg gcttgttgac acaacaaaca ctgtgattaa  11580
gattgcactg actaggaggc ccctcggcat caagaggttg atgcggataa tcaattactc  11640
gagcatgcat gcgatgttat tcagagatga tgtttttttg cccaacaggt ccaaccaccc  11700
cttagtctcc tctaatatgt gttcgctgac gctagcagat tatgcacgga acagaagctg  11760
gtcaccattg acagggggta ggaaaatact gggcgtgtct aatcccgata ccatagagct  11820
tgtagagggg gagattctta gtgtcagcgg agggtgcaca aagtgtgaca gcggagatga  11880
acagtttacg tggttccatc ttccaagcaa tatagagctg accgatgaca ccagaaagaa  11940
tcccccgatg agagtgccat atctcggatc aaagactcaa gagaggaggg ctgcctcgct  12000
tgcaaaaata gctcatatgt cacctcatgt gaaggcagca ctaagggcat catccgtgct  12060
aatctgggcg tatggggaca acgaagtaaa ctggactgcc gctcttcaga ttgcaaggtc  12120
tcggtgcaat ataaactcag agtatcttcg actattgtca cccctaccta cagctgggaa  12180
tctccaacat agattggatg atggcataac ccaaatgaca tttacccctg catctctcta  12240
tagggtatca ccttacattc acatatccaa tgattctcaa aggctattta ccgaagaagg  12300
aatcaaagag gggaatgtgg tttaccaaca aattatgctc ttaggtttat ctctaattga  12360
atcactcttc ccaatgacga caaccaagac atatgatgaa atcacattac acctccacag  12420
taaatttagt tgctgtatca gggaagcacc tgttgcagtt cctttcgagc tcctcgggtt  12480
ggcaccagag ttaaggacag taactacaaa taagttcatg tatgatccta gccctgtatc  12540
ggagagagac tttgcaagac ttgacctagc tatcttcaag agttacgagc ttaatttgga  12600
gtcataccoc acaatggagc taatgaacat tctttcaata tctagtggga agttgattgg  12660
tcagtccgtg gtttcctatg acgaagatac ctctatcaag aatgacgcca taatagtgta  12720
tgataataca cgaaattgga tcagtgaagc ccagaattca gatgtggtcc gcctattcga  12780
gtatgcagca ctcgaagtgc tcctcgactg tgcttatcaa ctctactatc tgagagtgag  12840
aggcctaaac aacatcgtcc tatacatgag tgatttatac aagaatatgc caggaattct  12900
actctccaat attgcggcca cgatatctca ccccatcatt cattcaaggt tgaatgcagt  12960
aggtctagtc aaccatgacg ggtcacatca gcttgcagac acagatttca tcgaaatgtc  13020
tgcgaaactg ttagtctctt gcactcgacg cgtggtatca ggtttatacg cagggaataa  13080
gtacgatctg ctgtttccat ctgtcttaga tgataacttg agtgagaaga tgcttcaact  13140
gatttcccgg ttatgttgtc tgtacacagt gctctttgct acaacaagag aaatcccaaa  13200
aataagaggc ctatcggcgg aagaaaaatg ctcagtactc actgagtacc tactgtcaga  13260
tgctgtgaaa ccattgcctg ggtccgaaca ggtgagctct atcatgtctc ccaacataat  13320
tacattccca gccaacctat attacatgtc taggaagagc cttaacttaa tcagagaacg  13380
agaggacaaa gataccatct tggcattatt gttccctcag gaaccgctac ttgagtttcg  13440
tccattacaa gatattggtg cgcgagtgaa agatccattt actcgacaac ctgcagcgtt  13500
catacaggag ttagatttga gtgctccagc aaggtacgat gcatttacac ttgatgagtt  13560
tcaccttgag cacacactgc cgaacccaga ggaagattac ttagtacgat acttgttcag  13620
aggaataggg actgcttcat cttcttggta taaggcatct catcttcttt ctgtacctga  13680
```

-continued ggtcagatgt gcaaggcatg gaaactccct atacttggcg gaaggaagtg gagccattat 13740
gagtcttctt gaactgcata taccgcacga gaccatctac tataatacgc ttttctcaaa 13800
tgagatgaac cccccacagc gacatttcgg accaactccg acacagtttc taaattcggt 13860
cgtttatagg aatctacagg cagaagtgcc atgtaaggat ggatttgtcc aggagtttcg 13920
ccccttatgg agagagaatg cagaagaaag tgacctgacc tcagataaag cagtagggta 13980
tatcacatct gcggtgccat acagatctgt atcattacta cattgcgaca ttgaaattcc 14040
tccaggatcc aatcaaagct tactagatca actggctacc aacttatccc tgattgccat 14100
gcactctgta agagagggcg gtgtcgtgat catcaaagta ttgtatgcaa tgggatacta 14160
cttccatctg ctcgtgaatt tattcactcc ttgttccaca aaagggtata ttctctctaa 14220
tggctatgcc tgtagagggg atatggagtg ttacctgata ttcgtcatgg gctatgtagg 14280
cggacctaca ttcgtgcacg aagtggtgag aatggcaaaa actctaatac agcggcacgg 14340
tacgcttctg tcaaaatcag acgaaattac gttgactagg ttatttacct cacagcagca 14400
tcgtgtaatg gacattttat ccagtccttt accgagactg atgaaattct tgagagagaa 14460
cattgatgct gcattgattg aagccggggg gcagcctgtc cgtccattct gtgcagagag 14520
tttagtgagc acactaacag atatgactca gatgactcag atcatcgcca gccacattga 14580
tacagtcatt cgatctgtga tctacatgga agctgagggt gaccttgctg acacagtgtt 14640
cttatttact ccttacaatc tttctacaga cggtaaaaag agaacatcac ttaaacagtg 14700
cacaagacag atcctagagg tcacaatact aggtcttaga gtcaaagatc tcaataaagt 14760
gggtgatgta ataggcttag tactcagagg tacagtttct ctggaggatc tcattccact 14820
gaggacatat ttgaagcgta gtacctgccc aaaatacttg aaggcagtcc tgggtattac 14880
taaactcaaa gaaatgttca cagacacctc tttattatac ctgactcgtg ctcaacaaaa 14940
attctatatg aaaaccatag gcaatgcggc caagggatat tacagcaata atgattccta 15000
aaggcgatca catatgaata ggttctcttc ctagccaact gtgtcctcat aaacctgatc 15060
ataccgtatt agaaaaaagt tgaattccga gtctttggaa ctcgtattcg gattctaata 15120
attatcttta aacggaagta tgcgtagttg ttcttgacta taggcctgtc gttcaccaaa 15180
tctttgtttg gt 15192

<210> SEQ ID NO 3
<211> LENGTH: 15192
<212> TYPE: DNA
<213> ORGANISM: Newcastle disease virus

<400> SEQUENCE: 3
accaaacaga gaatcggtga gttacggtaa aaggcgaaga agcaatcgaa atcgtacggg 60
tagaaggtgt gaacctcgag tgcgaggccg aaactcaaac ccgagggaac cttctgccgg 120
catgtcgtcc gtctttgacg aatacgagca gctcctcgct gctcagaccc gccctaacgg 180
agctcacgga ggaggagaga gagggagcac tttgaaagtt gaggtcccag tattcactct 240
taacagtgat gatccagagg atagatggaa ttttgcggta ttctgtcttc ggattgctgt 300
tagcgaggat gccaacaagc cgctcaggca aggtgctctc atatccctcc tatgctccca 360
ttctcaggtg atgagaaacc atgttgccct tgcagggaaa cagaacgagg ccacactggc 420
tgttcttgag atcgatggtt ttaccaatag tgtgccccaa ttcaacaaca ggagcggagt 480
gtctgaggag agggcacaga gattcctggt gatagcagga tctcttcccc gggcatgcag 540

-continued

```
taacggcact ccgttcgtta cagctggagt tgaagatgat gcgccagaag atatcactga    600
cactctggaa agaatcctat ctatccaggc ccaggtatgg gtcacagtag caaaggccat    660
gactgcatat gagacagcag atgagtcaga aacaagaagg atcaataagt atatgcagca    720
aggtagagtc cagaagaagt atatcctcca ccccgtatgc aggagtgcaa ttcaactcac    780
aatcagacat tctctggcag tccgcatttt cttagttagt gagcttaaga gaggccgcaa    840
tacggcaggt gggagctcta catattacaa cttagttggg gatgtagact catacatcag    900
gaacaccggg cttactgcat tcttcctgac actcaagtat ggaatcaata ccaagacatc    960
agctcttgca ctcagcagcc ttacaggtga tatccaaaaa atgaaacagc tcatgcgttt   1020
atatcggatg aaaggagaga atgcaccgta tatgacattg ttaggtgaca gtgaccagat   1080
gagctttgca ccagctgagt atgcacaact ttattctttt gccatgggca tggcatcggt   1140
cttagataag ggaactggta aataccaatt cgccagagac tttatgagca catcattctg   1200
gagacttggg gtggagtatg cccaggctca gggaagtagc atcaatgagg acatggctgc   1260
tgagctgaaa ctaaccccgg cagcaaggag aggtctggca gctgctgccc aacgagtatc   1320
cgaggaaatt ggcagtgtgg acattcctac tcaacaggcc ggggttctca ctgggctcag   1380
cgacgaaggc ccccgagccc cacagggtgg atcgagcaag tcgcaggggc aaccggatgc   1440
tggggacggg gaggcccaat tcttggattt gatgagagca gtggcgaata gcatgcgaga   1500
agcgccaaac tccgcacaga gcaccactca tccggagccc ccctcaactc ctgggccatc   1560
tcaagacaat gacaccgact gggggtactg atcgacaaca cccagcccgc cctcacaggg   1620
tcatcccaaa ccctccgccc gaatctctcc caaactcccc gattcacagc tctgcatggc   1680
caaaccaaca agagcacccc cccaccctct cttccaccct caaccacacg atcccgcccg   1740
cccaaagcag cacaggcata cctcggccca ccaagaatcc atgcagggcc caagatatta   1800
gaaaaaaata cgggtagaag agagacaccc agagatcagg acaagtcacc aaggtctccg   1860
ctctcccttc tacccagtgg actagggtga agatggccac ctttacagat gctgagatag   1920
acgatatact tgagaccagt ggaactgtca ttgacagcat aattacggcc cagggcaaat   1980
cagcagagac tgtcgggagg agcgcaatcc cgcaaggcaa gaccaaagcc ctgagcacag   2040
cacgggagaa gcatgggagc atccagccat ccgccggcca ggacacctcc gaccaacagg   2100
atagatcaga caaacagcca tccacacctg agcaggcgac ccccacacaac aactcaccgg   2160
ccacatccat cgaaccgctc cctactcagg ccgcaggcga ggccggcgac acacagctca   2220
ggaccggagc aagcaactct ctcttgtcca tgcttgacaa gctgagcaat aaatcgtcta   2280
atgctaaaaa ggggccacgg tcgagccccc aggaaggaca tcatcaacct ccggcccaac   2340
agcacgggaa tcaaccgagc cgtggaaaca atcaggaaag accgcagcac caggccaaat   2400
ccgcccctgg aagccggggc acagacgcga gcacagcata tcatggacaa tggaaggagt   2460
cacaactatc agctggtgca accccctcgtg tgctccagtc agggcagagc caagacagta   2520
cccctgcacc tgtggatcat gtccaactac ctgtcgactt tgtgcaggcg atgatgtcta   2580
tgatggaggc gttatcacag aaagtaagta aagttgacta tcagctagac ctagtctcaa   2640
agcagacatc ctccatccct atgatgcgat ctgaaatcca acagcttaaa acatctgttg   2700
cgatcatgga agccaattta ggaatgatga aaattctgga ccctggttgt gctaacgtct   2760
catccttaag tgatctacgg gcggtcgccc gatcccaccc agttttagtc tcaggccctg   2820
gagatccatc cccttacgtg acacaagggg gtgaaatgac actcaataaa ctctcgcaac   2880
cggtacagca cccttctgaa ttaattaaat ctgccacggc aagcgggcct gatatgggcg   2940
```

-continued

```
tggagaagga cactgtccgt gcattaatca cctcgcgccc gatgcatcca agctcctcag   3000
ctaagctcct gagtaagctg gatgcagcca ggtcgattga agagatcaga aagatcaaac   3060
gccttgcgct gaatggttga tcgccatcac aacttacaac aggctcctgc ctcattagtg   3120
tcacaaggaa tccttcctga gcccccccc acaaacccgc gctccaacac tccaagcaac   3180
gaccctctct cgccccccctt acttccccga atgatcgcgc aactgcaatt aatctaacag   3240
cattagagat taagaaaaaa tacgggtaga atcaaagcgc cccgactgtg ccaaaatgga   3300
ctcatccagg acaatcgggc tgtactttga ttctgccctc ccttccagca gcctgttagc   3360
attcccgatc gtcctacaag acacaggaga tgggaagaag caaatcaccc cacaatacag   3420
gatccagcgt cttgactcgt ggacagacag taaggaagac tcggtattta tcaccaccta   3480
cggattcatc ttccaaattg ggaatgaaga agtcaccgtc ggcatgatca acgacaatcc   3540
caggcacgag ttactttctt ctgcgatgct ctgcctagga agtgtcccga acgatggaga   3600
tcttgttgaa ctggcgaggg cctgcctcac tatggtggta acttgcaaga agagtgcgac   3660
taatactgaa agaatagtct tctcagtagt gcaggcacct cgggtgctgc aaagctgtat   3720
ggttgtggca aataggtact catcagtgaa tgcagtgaag catgtgaaag cacccgagaa   3780
gatccctggg agcggaaccc tagagtataa ggtgaatttt gtctctttga ctgtggtgcc   3840
gaggaaagac gtctatagga tcccaactgc agcattgaaa atatctggct caagcctata   3900
caatctcgcg ctcaatgtca ctattgatgt ggaggtagac ccgaagagcc cgttagtcaa   3960
atccctttct aagtctgata gtggatacta tgctaatctt tttttgcata tcgggcttat   4020
gtccactgta gataagaagg gaaagaaagt gacatttgac aagatagagg gaaagataag   4080
aagactcaat ctatctgtcg ggctcagtga tgtgctcgga ccttctgtgc ttgtgaagcc   4140
gagaggtgca cggactaagc tactggcacc tttcttctct agcagtggga cagcctgcta   4200
tcctatagca aatgcctctc cccaggttgc taaaatactc tggagccaaa ctgcgcacct   4260
gcggagtgta aaagtcatca ttcaagctgg cacccaacgt gctgtcgcag tgactgctga   4320
tcatgaggtt acctctacca agatagagaa gaaacacacc attgctaaat acaatccttt   4380
caaaaagtaa gttgcatccc tgagactgcg atccacccgc tttcctgaat catcatgaca   4440
caaaaaacta atctgtcttg attatttaca gttagtttac ctgtctatca agttagaaaa   4500
aacacgggta gaagattctg gatcccggtt ggcgccctcc aggtgcaaga tgggctccag   4560
accttctacc aagaacccag cacctatgat gctgactatc cgggttgcgc tggtactgag   4620
ttgcatctgt ccggcaaact ccattgatgg caggcctctt gcagctgcag gaattgtggt   4680
tacaggagac aaagccgtca acatatacac ctcatcccag acaggatcaa tcatagttaa   4740
gctcctcccg aatctgccca aggataagga ggcatgtgcg aaagccccct tggatgcata   4800
caacaggaca ttgaccactt tgctcacccc ccttggtgac tctatccgta ggatacaaga   4860
gtctgtgact acatctggag gggggagaca ggggcgcctt ataggcgcca ttattggcgg   4920
tgtggctctt ggggttgcaa ctgccgcaca aataacagcg gccgcggccc taatacaagc   4980
caaccaaaat gccgccaaca tcctccggct taaggagagc attgctgcaa ccaatgaggc   5040
tgtgcatgag gtcaccgacg gattatccca actagcagtg gcagttggga agatgcagca   5100
gtttgttaat gaccagttta ataaatacggc gcgtgaattg gactgtataa aaattacaca   5160
acaagttggt gtagaactca acctatacct aactgaactg actacagtgt tcgggccaca   5220
aatcacttcc cctgccctga ctcagctgac tatccaggca ctttataatt tagctggtgg   5280
```

-continued

```
caacatggat tacttattga ctaagttagg tgtagggaac aatcaactca gctcattaat   5340
tggtagcggc ttgatcaccg gcaaccctat actgtatgac tcacagactc aactcttggg   5400
catacaggtg aatttaccct cagtcgggaa cctgaataat atgcgtgcca cctacttgga   5460
gaccttatct gtaagcacaa ccaaagggtt tgcctcagca cttgtcccaa aggtagtgac   5520
acaagtcggt tccgtgatag aagaacttga cacctcatac tgtgtcgaat ccgatttgga   5580
tttatattgt acaagaatag tgacattccc catgtctcct ggtatttatt cctgtttgag   5640
cggtaataca tcagcttgca tgtattcaaa gactgagggc gcactcacta cgccatatat   5700
ggccctcaaa ggctcagtta ttgccaattg caagatgaca acatgtagat gtgcagaccc   5760
cccaggcatc atatcacaaa attatggaga agctgtatct ctgatagata gacattcatg   5820
caatgtctta tcattagatg ggataaccct gaggctcagt ggggaatttg atgcaactta   5880
tcaaaagaat atctcaatac tagattctca agtcatcgtg acaggcaatc ttgatatatc   5940
aactgagctt gggaatgtca acaattcaat aagcgatgcc ttggacaggt tagcggaaag   6000
caacagcaag ctagacaaag tcaacgtcag actaaccagc acatctgctc tcattactta   6060
tatcgttcta actgtcatat ctcttgtttt cggtgcactt agcctggttt tagcatgcta   6120
cctgatgtac aagcaaaagg cacaacaaaa gaccttacta tggcttggga ataataccct   6180
cgatcagatg agagccacta caagaacatg aatgcagatg agaggcggat atatccccaa   6240
tagcaacttg tgtgtcaatt ctgacagcct gttaatttaga agacttaaga aaaaactact   6300
ggatataagc aaccaaaggg caatacacgg gtagaacggt cggagaggcc acccctcatt   6360
caggaaccag gcttcacaac atctgttcta ccgcatcacc agtagcagat ttcagtcatg   6420
gaccgtgcag ttagcagggt tgtgctagag aatgaagaaa gagaagcgaa aaacacatgg   6480
cgcttggttt tccggatcgc agttttactt ttaatagtaa tgactttaac tatctctgca   6540
gccgccctgg tatacagcat gggggctagt acgccgcgcg acctcgcagg catatcgact   6600
gcgatctcta agacagagga taagattacg tctttactta gttcaaatca agatgtagta   6660
gataggatat ataagcaagt ggccctcgaa tctccgctgg cgctgctaaa tactgaatct   6720
ataattatga atgcaataac gtctctctct tatcaaatta acggggctgc gaataatagc   6780
gggtgtgggg cgcctgttca tgatccagat tatatcgggg ggataggcaa agaactcata   6840
gtagacgaca ctagtgatgt cacatcattc tatccttctg cataccaaga acacctgaat   6900
tttatcccgg cgcctactac gggatcaggt tgcactcgga taccctcatt tgacatgagc   6960
gctacccact actgttatac tcacaatgtg atacttgctg gttgcaggga tcactcacac   7020
tcacatcaat acttggcact tggtgtgctt cggacatctg caacagggag ggtattcttt   7080
tctactctgc gttccatcaa tttagatgac acccaaaatc ggaagtcctg cagtgtgagt   7140
gcaactcctc taggttgtga catactgtgc tctaaagtca cagagactga ggaagaggat   7200
tataagtcag ttacccccac gtcaatggtg cacggaaggt tagggtttga cggtcaatat   7260
catgagaagg acctagacat cacagtctta tttaaggatt gggtggcaaa ttacccggga   7320
gtgggaggtg ggtcttttat tgacgaccgt gtatggttcc cagtttacgg agggctaaaa   7380
cccaactcgc ctagcgacac tgcacaagaa gggaaatatg taatatacaa gcgctataat   7440
aacacatgcc ccgatgaaca agattaccaa attcggatgg ctaagtcttc gtacaagcct   7500
gggcggtttg gtggaaagcg cgtgcagcaa gccatcttat ctatcaaagt gtcaacatct   7560
ttgggtgagg acccggtgtt gactgttccg cctaatacaa ttacacttat gggggccgaa   7620
ggcagagttc tcacagtagg gacatctcat ttcttgtacc aacgagggtc ttcatatttc   7680
```

-continued

```
tcccctgcct tactatatcc tatgacagta tacaacaaaa cagctactct tcatagtcct   7740
catacattca atgctttcac ccggccaggt agtgtccctt gtcaggcatc agcgagatgc   7800
cctaactcat gtatcactgg agtctatact gatccgtatc ctttagtctt ccataagaat   7860
cataccttgc gaggggtctt cgggacaatg cttgacaatg aacaagcaag actcaaccct   7920
gtatctgcag tattcgacag catatcccgc agtcgtgtaa cccgggtgag ttcaagcagc   7980
accaaagcag catacacgac atcgacatgt tttaaagttg tcaagaccaa taaagcttat   8040
tgtcttagca ttgcagaaat atctaatacc ctattcgggg aattcaggat cgttccttta   8100
ctagttgaga ttcttaagga tgatagggtt taagaagcta gatctggccg gttgagtcga   8160
acacaggatg gttgggaaga tgatgctgta tcacctatct ctcacaatgc caaggagcaa   8220
actgaatatc aatgcaagcc cgaatcctat actgccgggc ggctataatc tgataatgct   8280
gatgtgatca gtctgaatct tgtccatagt cactttatta agaaaaaata tgaaaggtag   8340
tgagatataa ggggaaacaa catacagagg atagcacggg taggaaatgg cgggctccgg   8400
tcccgaaagg gcagagcacc agatcatcct accagagtca catctatctt ctccattggt   8460
caagcacaaa ttgctctatt actggaaatt aactgggcta ccgctccctg acgaatgcga   8520
ctttgatcat ctcattatca gcaggcaatg gaagaaaata cttgaatctg ccactcctga   8580
cactgagaga atgataaaac tcgggcgggc agtgcaccag actctcaacc acaactccaa   8640
gataactgga gtactccatc ccaggtgttt agaagaactg gctagtattg aggtccctga   8700
ttcaaccaac aaatttcgga agatcgaaaa gaagatccag attcacaaca cgaggtatgg   8760
agacctgttc acaaagctat gcacgctcat tgaaaagaaa ttgctaggat catcccggtc   8820
tagcaatgtc ccacgatcag aggagttcag cagcatccgt acagatccgg cattctggtt   8880
tcactcaaaa tggtccagag ccaagtttgc atggctccat ataaaacagg tccagaggca   8940
tctgattgta gcagcaagaa caaggtccgc agtcaacaag ttagtgacgc taacccatag   9000
ggtaggccaa gtctttgtta ctcctgagct tgtcattgtg acacatacag atgagaacaa   9060
gttcacatgc ctcacccaag aacttgtatt gatgtatgca gatatgatgg aaggcaggga   9120
catggtcaac ataatatctt ctacggcgac acatctcagg agtctatcag agaaaattga   9180
tgatattctg cggttagtag atgctctggc aaaggatttg ggcaatcaag tctatgatgt   9240
tgtagcatta atggagggat tcgcatacgg tgccgttcag ctgcttgagc cgtcgggtac   9300
atttgcagga gatttctttg cattcaacct acaggagctc aaggacactc taatcgaact   9360
cctcccaaat gatatagcag aatcagtaac tcacgcaatc gccaccgtat tctctggctt   9420
agaacagaat caagcagctg agatgttgtg cttgctgcgt ttgtggggtc atccactgct   9480
tgaatcccgt agtgcagcaa aagcagtcag gagccagatg tgcgcaccga agatggtgga   9540
cttcgatatg atcctccagg tattatcctt ctttaaggga acaatcatca atggatacag   9600
aaagaagaac tcaggtgtgt ggccacgcgt caagatagat acgatatacg ggaaggtcat   9660
tgggcagcta catgctgatt cggcagagat ttcacatgat gtcatgttga gagagtacaa   9720
gagtttatct gcccttgaat tcgagccatg tatagaatat gaccctgtca ccaatctgag   9780
tatgttctta aaggacaagg caatcgcaca tccaaaagat aactggctcg cctcatttag   9840
gcggaacctt ctctctgagg accagaggaa acaggtaaag gaggcaacct caactaaccg   9900
cctcttgata gagttcctag aatcaaatga ttttgatcca tataaggaga tggaatactt   9960
gacaaccctt gagtacctaa gagatgacag tgtggcagta tcatactcac tcaaagagaa  10020
```

-continued

```
ggaggtgaaa gttaatgggc ggattttcgc taagttaaca aagaaattaa ggaactgcca  10080
ggtaatggca gaaggaattc tagctgacca gattgcacct tttttccagg gaaatggggt  10140
cattcaagat agcatatcct tgactaagag tatgttggcg atgagtcaac tgtcctttaa  10200
cagcaataag aaacgtatca ctgactgcaa agagagggtt tcctcaaacc gcaatcatga  10260
tccgaagagc aagaatcgtc ggagagttgc cacctttatc acgactgacc tgcaaaagta  10320
ttgtcttaac tggagatatc agacaattaa gctattcgcc catgccatca atcagctgat  10380
gggcctacct cacttcttcg agtggattca tcttagacta atggacacta caatgtttgt  10440
aggagaccct ttcaatcctc caagtgaccc gaccgactgt gatctatcaa gagtcccaaa  10500
tgatgatata tatattgtca gtgctagagg gggcattgag gggctatgcc agaagctatg  10560
gacaatgatc tcaattgctg caatccaact tgctgcagca aggtcgcatt gtcgagttgc  10620
ctgtatggta caaggtgaca atcaagtaat agctgtgacg agagaagtaa gatcagatga  10680
ctccccggat atggtgttga cacagttgca tcaagctagt gataatttct tcaaagaact  10740
gattcatgtc aatcatctga ttggccataa cctgaaagat cgtgaaacca tcaggtcaga  10800
cacgttcctc atatacagca aacgaatatt caaagacgga gcaatactca gtcaggtcct  10860
caaaaactca tctaaattag tgctaatatc aggcgacctt agtgaaaaca ctgtaatgtc  10920
ctgtgccaac attgcatcca ctgtagcacg gctgtgtgag aacgggctcc ctaaggactt  10980
ctgttattat ttaaattatc taatgagttg cgtgcagaca tactttgatt ctgagttttc  11040
tattactcac agttcgcaac cagattccaa ccagtcttgg attgaggaca tctctttcgt  11100
acactcatac gtcttaaccc ctgcgcagct gggaggactg agtaaccttc aatactcaag  11160
gctctacaca aggaatattg gtgacccggg gactactgct tttgcggagg tcaagcgatt  11220
agaagcagtg ggttgctga gtcctagcat tatgactaac atcttaacta ggccacctgg  11280
caatggagac tgggccagcc tgtgcaacga tccatactct tttaattttg agactgtcgc  11340
aagcccaaat attgtcctta agaaacatac acagaaagtc ttatttgaga cttgttcaaa  11400
ccctttatta tccggagtac atacagagga caatgaggca gaagagaagg cactggctga  11460
attcctactc aatcaagaag cggttcaccc acgtgtcgca catgctatca tggaagcaag  11520
ctctgtaggt aggagaaagc aaatccaagg gcttgttgac acaacaaaca ctgtgattaa  11580
gattgcgctg actaggaggc ccctcggtat caagaggctg atgcggatag tcaattactc  11640
gagcatgcat gcaatgttat tcagagacga tgttttctta tctaatagat ccaaccatcc  11700
attagtctct tctaatatgt gttcgctgac gctagcagat tatgcccgga acagaagctg  11760
gtcacctttg acaggaggta ggaaaatact gggtgtatct aaccccgata ccatagaact  11820
tgtggaggga gagattctta gtgtcagtgg ggggtgcaca aaatgtgaca gcggagatga  11880
acagtttact tggtttcatc ttccaagcaa tatagagctg actgatgaca ccagcaagaa  11940
tccccccgatg agagtgccat atctcgggtc aaagacccaa gagaggaggg ctgcctcgct  12000
tgcgaaaata gctcatatgt cgccacatgt aaaggcagca ctaagagcat cgtccgtgtt  12060
aatctgggct tatggggaca acgaagtaaa ctgggctgct gctcttaaga ttgcaaggtc  12120
tcgatgtaac ataagcccag agtatcttcg gctattgtca cccctgccca cagctgggaa  12180
tctccaacat agattggatg atggcataac ccagatgaca tttacccctg catctctcta  12240
cagagtatca ccttacattc acatatccaa tgattctcag aggctattta ctgaagaagg  12300
aatcaaagag gggaatgtgg tttatcaaca aattatgctc ctgggtttat ctctaattga  12360
atcactcttc ccaatgacaa caaccaagac gtatgatgag attacattac acctccacag  12420
```

```
taaatttagc tgctgtatca gggaagcacc tgttgcggtt cctttcgagc tactcgggtt  12480
ggcaccagaa ttaaggacgg taacctcaaa taagttcatg tatgatccta gccctatatc  12540
agagagagat tttcgagac ttgacttagc tatcttcaag agttacgagc ttaatttaga  12600
gtcgtattcc acaatagagc taatgaacat tctttcaata tctagtggga agttgattgg  12660
tcagtccgtg gtttcctatg atgaagatac ctctataaag aatgacgcta taatagtata  12720
tgacaacaca cggaattgga tcagtgaagc ccagaattca gatgtggtcc gcctattcga  12780
gtatgcggca ctcgaagtgc tcctcgattg ttcttaccaa ctctactatc tgagagtgag  12840
aggtctaaac aacattgtcc tatacatgag tgacttatac aagaatatgc cagggatttt  12900
actctccaat attgcggcca cgatatccca ccccatcatt cactcaaggt tgaatgcagt  12960
aggtctagtc aaccatgacg ggtcacacca gcttgcagac acagatttca tcgaaatgtc  13020
tgcgaaactg ttagtctctt gcactcggcg cgtggtctca ggcttatatg cagggaataa  13080
gtatgatctg ctgtttccat ctgtcttaga tgataacctg agtgagaaga tgcttcagct  13140
gatttcccgg ttatgctgtc tgtacacagt gctttttgct accacaagag aaatcccaaa  13200
aataaggggc ctatcagcgg aagaaaaatg ctcaatactc actgagtacc tactgtcaga  13260
tgctgtgaaa ccattgctta ggcccgaaca attgagctct atcacgtctc ccaacataat  13320
tacgttccca gccaatctat attacatgtc taggaagagc cttaatttga tcagggaacg  13380
agaagacaga gataccatct tggcattgtt gttcccccag gaaccactgt ttgagcttcg  13440
tccagtacaa gacattggtg ctcgagtgag agatccattt actcgacaac ctgcatcatt  13500
catacaagag ttagatctga gtgctccagc aaggtatgac gcatttacac ttagtgaggt  13560
tcactccgag cacacattgc cgagcccaga ggaagattac ttagtacgct acttgttcag  13620
gggaataggg actgcctcat cttcttggta taaggcatct catcttcttt ccgtacctga  13680
ggtcagatgt gcaagacatg ggaactcctt atacttggcg gaaggaagtg gagcaatcat  13740
gagtcttctt gaattgcata taccgcacga gaccatctat tataatacgc ttttctcgaa  13800
tgagatgaac cctccacagc gacatttcgg accgacccca acacagtttc taaattcagt  13860
cgtttatagg aacctacagg cggaagtgcc atgcaaagac ggattcgtcc aggagttttg  13920
cccattatgg agggagaatg cagaagaaag tgacctgacc tcggataaag cagtgggata  13980
tatcacatct gtggtgccct ataggtctgt atcattacta cattgtgaca ttgaaattcc  14040
tccagggtcc agtcaaagct tactagatca actggctact aatttatctc tgattgccat  14100
gcattctgta agggagggcg gggtagtgat cataaaagta ctgtatgcaa tgggatacta  14160
cttccatcta ctcatgaatt tattcactcc atgttccaca aaaggatata ttctctctaa  14220
cggttatgcc tgtagagggg atatggagtg ttacctgata tttgtcatgg gctatttagg  14280
cgggcctaca ttcgtgcatg aggtggtgag gatggcaaaa actctaatac aacggcacgg  14340
tactcttttg tctaaatcag atgaaattac attgactagg ctatttacct cacagcagca  14400
tcgtgtaata gacatcctat ccagccctct accgagacta atgaagttct tgagagaaaa  14460
tattgatgct gcgctgattg aagcgggggg acagcccgtc cgtccattct gcgcagagag  14520
tttagtgagc acattaacag atatgactca gatgactcag gtcattgcca gccacattga  14580
cacagtcatt cgatctgtga tttacatgga ggctgagggt gaccttgctg acacagtgtt  14640
cttatttact ccttacaatc tctctacaga tggtaaaaag agaacatcac tcaaacagtg  14700
cacaagacag atcttagagg tcacaatact gggtctcaga gtcaaagatc tcaataaagt  14760
```

-continued

```
aggtgatgta attggcttaa tactcagagg tatggtttct ctggaggacc tcatcccact  14820
aaggacatac ctgaagcgca gtacctgtcc gaagtatttg aaggcagtcc taggtattac  14880
taaacttaaa gaaatgttca cagatacctc cttactatac ttgactcgtg ctcaacaaaa  14940
attctacatg aaaactatag gtaatgcagc caagggatat tacagtaaca atgactctta  15000
aaggcaatca cacattaata aactatcttc ttaaccgatt gtttcctcgc tgatttgatt  15060
ataccatatt agaaaaaagt tgaattccga ttctttgaaa ctcgtattcg gattcaatta  15120
attatcttaa aacagcagtg aacgtagttg tccttaatta tagtcctgtc attcaccaaa  15180
tctttgtttg gt                                                      15192
```

<210> SEQ ID NO 4
<211> LENGTH: 15132
<212> TYPE: DNA
<213> ORGANISM: Newcastle disease virus

<400> SEQUENCE: 4

```
accaaacaga gaatcggtga gttacgataa aaggcgaaga agcaatcgaa atcgtacggg     60
tagaaggtgt gaacctcgag tgcgaggccg aaattcaaac tcgaggaagc cttctaccga    120
catgtcgtcc gtatttgacg aatacgagca actcctcgct gctcagactc gcccgaatgg    180
agctcacgga ggaggagaga aagggagcac tttgaaagtt gaggtcccag tatttactct    240
taatagtgac gatccggaag atagatggaa tttttcggta ttctgtcttc ggattgctgt    300
tagtgaggat gccaacaagc cactcaggca aggtgctctt atatccctct tgtgctccca    360
ttcccaagtg atgaggaacc atgttgccct tgcagggaaa cagaatgagg ctacgctggc    420
gattcttgag attgatgggt ttgctaacag cacacctcag ttcaacaaca ggagtggagt    480
gtccgaggag agagcacaga gatttatggt gatagccggg tcgctccctc gggcatgcag    540
caacggtact ccgttcgtca cagccggggt tgaagatgat gcaccagaag atatcactga    600
cactctggaa aggatcctat ctatccaggc tcagatatgg gtcacagtag cgaaggctat    660
gactgcatat gagacagcag atgagtcaga aacaagaaga attaataagt atatgcagca    720
aggcagagtc caaaagaagt atatcctcca tcccgtatgc aggagtgcaa ttcaactcac    780
aatcaggcac tctttggcag ttcgcatttt cttagttagc gagcttaaga gaggccgcaa    840
tacggcaggt gggagctcca catattacaa cttagtaggg gatgtagact cgtacatcag    900
gaacactggg cttactgcat tcttcttgac actcaaatat ggaattaata cgaagacatc    960
agctctcgca ctcagcagcc tcacaggtga tatccaaaaa atgaagcagc tcatgcgttt   1020
atatcggatg aagggagaaa atgcaccgta catgacatta ctaggtgaca gtgaccagat   1080
gagctttgca ccagctgagt acgcacaact ttattctttt gccatgggca tggcatcagt   1140
cttagataaa ggaactggca aataccaatt cgccagggac tttatgagca catcgttctg   1200
gagacttggg gtggaatatg ctcaggctca ggggagtagc attaatgagg atatggctgc   1260
tgagctaaaa ttaaccccgg cagcaaggag ggggcctggca gctgccgctc aacgagtgtc  1320
tgaggaaatc ggcagcatgg atgttcctac tcaacaggcc ggggtcctca ccggactcag   1380
cgatgtaggc ccccaggcct cacagggcga atcgagcaag ccaaaagggc aaccgaatgc   1440
cggggacgga gagacccaat tcttggattt gatgagagcg gtggcaaaca gcatgcgaga   1500
agcacaaaac tctgcaccgg gcactacccc tccagagccc cccccaacac ctgggccatc   1560
cccagacaat gacaccgact gggggtactg attgacaaca cccagcccgc ccccacaggg   1620
ccaccccaaa tcccccgccc gaacccctcc ctcactcccc gacccacagc ctcgcatggc   1680
```

-continued

```
cgagccaacg acagcactcc cccattctct cctccacccc cagccgcaca accccacccg   1740
cccacaacaa cacagatgca acctgaccta ccagcggtcc atgcagagcc aaaggtatta   1800
gaaaaaaata cgggtagaag agagacgccc agagaccaag acaagtcacc aaggtctctg   1860
ttctcccttc tacccagtag accagggcga agatggccac ctttacagat gcggagatag   1920
acgatatact tgagaccagt ggtgccgtca ttgacagcat aatcacagcc cagggtaaac   1980
caacagagac cctcggaaag ggcgcaatcc agcaaggcga tacaaaagca ctgagcacag   2040
cacgggagaa acacggagac atccaatcac ccgctagtca ggactcccct gaccaacagg   2100
atgggtcagg caaacagccg tctacgccta agcaggcgac ctcacacaac agcccttcag   2160
ccacacccgc cgaatcgccc cccactcagg ccgcgggcga ggccggcgac acgcagctca   2220
agaccggagc aagcaactct cttttgtcca tgctagacaa gctgagcaat aaatcgtcta   2280
atactaaaaa gggctcacgg tcaagtcctc aaggaggaca tcaccaacct ctggccaaac   2340
aacatgggaa tcagctgaac cacgggaacc accagggaaa atctcagcac caggccaagg   2400
tcgcccctgg aagccggggc acagacgtga acatagcata tcatggacaa cagaaggagt   2460
cacaactatc agctggtgca atccctcatg cgctccaatc agggcagagc caagacaata   2520
ctcttgtatc tgtggatcat gtccagccac ctgtcgactt tgcgcaggca atgatgtcta   2580
cgatggaggc gttattgcag aaggtaaata gagttgacta tcagctagag ctaatcttga   2640
agcagacatc ctccatccct atgatgcgga ctgaaatcca acagttgaaa acatctgttg   2700
cagtcatgga ggccaattta ggcatgatga aaattctgga ccctggttgt gctaacattt   2760
catccttaag cgatctacgg gcagtcgctc gatcccaccc agttttagtt tcaggccccg   2820
gagatccgtc cccttatgtg acacaaggtg gcgaagtgac gctcaataag ctctcgcaac   2880
cagtacaaca cccttccgag ttaattaaac ccgccgcaac aagcggacct gacatgagtg   2940
tggagaaaga caccgtccgt gcattgatca cttcacgccc gatgcatccg agctcctcag   3000
ccaagctcct gagtaagcta gatgcagcca agtcgatcga ggagattagg aagatcaaac   3060
gccttgcgct gaatggttga tcaccatcac aatctacagc aggtccctgc ctccttagtg   3120
tcacaaggga tccgtcctag gccccttcct ataaatctac gttctagcac tccaagcaat   3180
gaacccottt agcttttttt accccattga atgatcgcgc aattacagtt aatctaacag   3240
cattgaagat taagaaaaaa tacgggtaga atcaaagtgc cctgactgtg ccaaaatgga   3300
ctcatccagg acaatcggac tgtactttga ttctgccctt ccctccagca gcctgcttgc   3360
tttcccgatc gtcctacaag ccacaggaga tgggaagaag caaatcaccc cacaatatag   3420
gatccaaagg ctagactcgt ggactgacag cagagaagat tcggtattta tcactaccta   3480
tggattcatc ttccaagtcg ggaatgaaga agtcaccgtc ggcatgatca atgataatcc   3540
aaggcaagag ttactctcct ctgcaatgct ctgcctaggg agtgtcccta atgacgggga   3600
ccttgttgag ctggcgaggg cctgccttac tatggtggtg acatgcaaga agagtgcaac   3660
caatactgag agaatagtct tctcgatagt gcaggcaccc cgggtgctgc aaagctgtat   3720
ggttgtggca aataggtact catcggtgaa cgcagtaaag catgtaaaag caccagagaa   3780
gatccccgga agcggaactc tagagtataa ggtgaacttt gtctctttga ctgtggtgcc   3840
acggaaggac gtctacagga tccctaccgc ggcattaaaa gtatctggct cgagcctgta   3900
caatcttgcg ctcaatgtca ctattgatgt ggaggtggct ccgaatagcc cattagtcaa   3960
atctctttcc aagtccgata gtggatatta tgctaacctt ttcttacata tcgggcttat   4020
```

-continued gtccactgtg gataaaaagg gaaagaaagt gacatttgac aagttggaaa agaagataag 4080
aagactcaat ctatctgtcg ggctcagtga tgtgctcggg ccttccgtgc ttgtgaaggc 4140
gagaggtgca cggactaagc tgttggcacc tttcttctct agcagtggga cagcctgcta 4200
ccctatagcc aatgcctccc ctcaggttgc taagatactc tggagtcaga ctgcgcacct 4260
gcgaagtgta aaggtcatca ttcaggcagg cacccaacgt gctgtcgcag tgactactga 4320
tcacgaggtt acctccacca agatagaaaa gaggcatact attgctaagt acaatccctt 4380
caagaaatag attgtattcc tgatgctatg gtctgctcgc tttcttgaac catcatgaca 4440
caaaaaacta atctgtcttg attatttaca gttagtttac ctgtctatca agttagaaaa 4500
aacacgggta gaagattctg gatcccggtt ggcgccctcc aggtgcaaga tgggctccag 4560
accttctacc aagaacccag cacctatgat gctgactatc cgggttgcgc tggtactgag 4620
ttgcatctgt ccggcaaact ccattgatgg caggcctctt gcagctgcag gaattgtggt 4680
tacaggagac aaagccgtca acatatacac ctcatcccag acaggatcaa tcatagttaa 4740
gctcctcccg aatctgccca aggataagga ggcatgtgcg aaagccccct tggatgcata 4800
caacaggaca ttgaccactt tgctcacccc ccttggtgac tctatccgta ggatacaaga 4860
gtctgtgact acatctggag gggggagaca ggggcgcctt ataggcgcca ttattggcgg 4920
tgtggctctt ggggttgcaa ctgccgcaca aataacagcg gccgcagctc tgatacaagc 4980
caaccaaaat gctgccaaca tcctccggct taaggagagc attgctgcaa ccaatgacgc 5040
tgtacacgag gtcactaacg gattatcaca actagcggtg gcggtcggga agatgcagca 5100
gtttgttaat aaccagttta ataatacggc gcaagaattg gactgcataa aaattgcaca 5160
acaagtgggc gtcgaactca atttgtatct aactgaattg accacagtgt tcgggccaca 5220
aatcacctcc cctgctttaa ctcagctgac tatccaggca ctttataatt tagccggtgg 5280
caatatggat tacctgttga ctaagttggg tgtagggaat aatcaactca gttcgttaat 5340
tggtagtggc ttgataactg gcaaccctat actatatgac tcacagaccc aactcttagg 5400
catacagata aatttaccct cagtcgggag cctaaataat atgcgtgcca cctacttgga 5460
gaccttatcc gtaagcacga ccaaagggtt cgcctcagca cttgtcccga aagttgtgac 5520
gcaagtcggc tctgtgatag aagaacttga cacctcatat tgtatagaat ccgatataga 5580
tctatattgt acaagggtag tgacattccc catgtctcct ggtatttact cctgtctgag 5640
cggcaatacg tcagcttgta tgtattcaaa gaccgaaggt gcactcacta caccatacat 5700
ggccctcaaa ggctcagtta ttgccaattg caagatgact acatgcagat gcgcagatcc 5760
cccaggtatc atatcacaga attatgggga agctgtgtct ctaatagata aacattcatg 5820
cagtgtcttg tccctagacg ggataactct gaggctcagt ggggaatttg atgcgaccta 5880
tcaaaagaac atctcaatac tagattctca agtcatcgtg acaggaaatc tcgatatatc 5940
aactgagctt gggaatgtta acaactcgat aagcagtacc ctggacaaat tagcagaaag 6000
caacaacaag ctaaacaagg tcaatgtaaa cctaaccagc acatctgctc tcatcactta 6060
tattgtctta gctatcgtat ctcttgcttt cggcgtaatt agcctggttc tagcatgcta 6120
cctgatgtat aaacaaagag cacaacaaaa gaccttacta tggctcggga acaacaccct 6180
tgatcagatg agagccacta caagaacctg aatacagatg agagatgaat gtatccccag 6240
taacaattcg tacgtcaatt ctgatagcct gccaattggg aaaattataa aaaaaccact 6300
ggatatgaat ggccgaagag caatacacgg gtagaacggt cggagaagcc accccttagt 6360
caggaaccag gcttcacaac gtccgttcta ccgcattacc gattgcagac ttcagtcatg 6420

-continued

```
gatcgtgtag ttagcagagt cgtactagaa aacgaagaaa gagaagcaaa gaatacatgg   6480
cgcctggttt tccgggtcgc agtcctatct ctaatagtaa tgacattagc tatctctgta   6540
gccgccctgg tatacagcat ggaggctagc acgccgaacg accttgcggg tatatcgacg   6600
gtgatctcca gggcagagga tagggttaca tctttactca attcaaatca agatgtggta   6660
gatagggtat ataaacaggt ggcccttgag tccccgctgg cgttgttgaa tactgagtct   6720
ataattatga atgcaataac ttctctttcc tatcaaatta atggggctgc aaatagtagt   6780
gggtgtgggg cacctgttca tgacccggat tatattgggg gggtaggtaa agagctcata   6840
gtagatgaca cgagtgatgc cacttcattc tatccttcag catatcaaga acacctgaac   6900
tttatcccgg cgcccaccac aggttcaggc tgcactcgga taccctcatt cgacatgagc   6960
gctacccact attgttatac tcacaatgtg atattatctg gctgcagaga tcactcacac   7020
tcacatcagt atttggcact aggtgtgctt cggacatctg caacagggag ggtattcttt   7080
tctactctgc gttccatcaa tttagatgac acccaaaatc ggaagtcttg cagtgtgagt   7140
gcaactcctt taggttgtga tatgctgtgc tctaaagtca cagagactga ggaggaggat   7200
tataagtcag ttacccccac atcaatggtg catggaaggt tagggtttga cggtcagtac   7260
catgagaagg acttagacgt cacagtctta tttaaggatt gggttgcaaa ttacccggga   7320
gtgggaggag ggtctcttat tgacgaccgt gtatggttcc cagtttatgg agggctaaaa   7380
cccaattcac ctagcgacac tgcacaagaa gggaaatatg taatatacaa gcgctataat   7440
aacacatgcc ccgatgaaca agattaccaa gttcggatgg ctaaatcctc gtataagcct   7500
ggacggtttg gtgggaagcg cgtacagcaa gccatcctat ctatcaaagt atcaacatct   7560
ttgggcgagg acccggtgct gactgtaccg ccaaatacag ttacactcat gggggccgag   7620
ggcagaatcc tcacagtagg aacatctcat ttcttgtacc agcgagggtc ttcatacttt   7680
tctcccgcct tactataccc tatgacagtg cgcaacaaaa cagccactct tcatagtcct   7740
tatacattta atgcgttcac tcggccgggt agtgtccctt gccaggcatc agcaaggtgc   7800
cctaactcat gtatcactgg agtctatact gatccgtacc ctgtagtctt ccataggaat   7860
cacaccttgc gaggggtgtt cgggacaatg cttgataatg aacaagcaag gctcaatccc   7920
gtatctgcaa tatttgacta cacatctcgc agtcgcataa cccgggtaag ttcgaccagc   7980
accaaggcag catacacgac atcgacatgt tttaaagttg tcaagactaa taaagtgtat   8040
tgtcttagca ttgcagaaat atccaatact ctatttgggg aattcaggat cgttccttta   8100
ctggtcgaga ttctcaaaga tgatagggtt taagaagcta agatcagcca gccgggtcca   8160
ccacgcggga tatgggacga tgacaccgta ccaaccttcc tctgtaatgc caaggatcaa   8220
gcagaacacc aatacgagcc caaatctcaa gctattgagc aaccgcaatc ggacaacgct   8280
gacgcgatcg gcctgaatct tgtcaatagt cactctgttt agaaaaaata tgagaggtgg   8340
tgggatataa agaaaaacaa cttacagcag atagcacggg taggacatgg cgggctccgg   8400
tcccgatagg gcagagcacc agattatcct accagagtca catctttctt ctccactagt   8460
caaacacaaa ttactctatt actggaaatt aactgggcta ccacttcctg atgaatgcga   8520
ttttgaccat ctcattatca gcaggcaatg gaaaaaaatc ctcgagtcag ccactcctga   8580
cactgagaga atgataaaac tcgggcgggc agtgcatcag actctcagcc acgattctaa   8640
gataaccgga gtgctccatc ctaggtgttt agaagaattg gctagtattg aaattcccga   8700
ctcaactaac aagtttcgaa agattgaaaa gaagatccag attcacaaca cgagatatgg   8760
```

-continued

```
agaaaagttc acgaggttgt gcacgcacgt tgaaaagaaa ttgctaggat catcctggtc   8820
tagcaatgtc ccacgatcag aggaattcaa cagcatccgt atggatccag ccttttggtt   8880
tcactcaaaa tggtccagag ccaagtttgc ttggctccat ataaagcaag tccagagaca   8940
tctgatcgta gcagcaagaa caaggtccgc agttaacaaa ctagtgacac tgactcataa   9000
aataggccaa gtctttgtta ctcctgagct tgtcattgtg acacatacag atgagaacag   9060
gttcacatgc ctcacccagg aacttgtatt gatgtatgcg gatatgatgg agggcaggga   9120
tatggtcaac ataatatctt ctacggcggc acatctcaga aacttatcag agaaaattga   9180
tgatgttctg cggttagtgg atgctctagc aaaagatttg ggcaaccggg tctatgatgt   9240
cgtatcacta atggagggat tcgcatatgg agccgttcag ttgctcgagc cgtcaggtac   9300
atttgcagga gactttttttg cattcaacct gcaggagctc aaagacactc taatcgaact   9360
cctcccaaat gatatagcag aatcaataac tcatgcaatc gccaccatct tttcgggctt   9420
agaacagaat caagcagctg agatgttgtg tttgctgcgc ttgtgggggc acccactgct   9480
tgagtcccgt attgcagcaa aagcagtcag gagccagatg tgtgcaccaa agatgctaga   9540
ctttgatatg atcctccagg tgttatcttt ctttaaggga acaatcatca atggatacag   9600
aaagaagaac tcgggtgtat ggccacgtgt caagatagat acgatatatg ggaatgtcat   9660
tagacagctg cacgctgatt cagcagagat ttcacatgat gtcatgttga gggaatataa   9720
gaatctatct gcccttgaat tcgagccatg catagattat gaccctgtga ccaacttaag   9780
catgttctta aaagacaaag caatcgcaca tcctaaagat aactggctcg cctcatttag   9840
gcgaaatctt ctctctgagg accaaaagaa acatgtaaag gaagcgacct caactaatcg   9900
cctcttgata gagttcctgg agtcaaatga ttttgatcca tataaggaga tggaatattt   9960
gacaaccctt gagtacctaa gagacgacaa tgtagctgtg tcatactccc tcaaagagaa  10020
ggaggtgaaa gtgaatgggc ggattttcgc taaattaacc aagaaattga ggaactgtca  10080
ggtaatggca gaaggaattc tcgctgacca aattgcacct ttctttcagg gaaatggggt  10140
cattcaggat agcatatcct tgactaagag tatgttagca atgagccaat tatcttttaa  10200
cagcaataag aaacgtatca ctgactgtaa ggaaagggtt tcctcaaacc gcaaccatga  10260
tccaaagaat aagaatcgcc gaagagtcgc cacttttatc acgactgatc tgcagaagta  10320
ctgtcttaac tggagatatc agacaatcaa gctatttgcc cacgccataa accagctgat  10380
gggcctacct cacttctttg agtggattca tcttagatta atggacacta cgatgtttgt  10440
aggagatcct ttcaatcccc ctagtgaccc tactgactgt gatctctcaa gagtcccaaa  10500
tgatgacata tatattgtaa gtgccagggg aggtattgag gggttatgtc agaagctatg  10560
gacaatgata tcgattgctg caatccaact tgccgcagca agatcgcatt gtagagttgc  10620
ctgcatggta caaggtgaca atcaggtaat agctgtaaca agagaggtaa ggtcagatga  10680
ctcctcagat atggcgttga cacagttgca ccaagccagt gataatttct tcaaagagct  10740
gatccatgtc aatcatctga ttggccataa cctaaaagac cgcgaaacta tcaggtcgga  10800
cacattcttc atatatagca agcgaatatt caaggatgga gcaatactca gtcaggtcct  10860
taagaactca tctaaattgg tactgatatc aggcgacctt agtgaaaata ctgtaatgtc  10920
ctgtgccaac attgcatcta ctatagcacg gctatgtgaa aacgggcttc ctaaggactt  10980
ctgttattat ttaaactacc taatgtgttg tgtacaaaca tattttgatt ctgaattttc  11040
cattactcac agctcacagc cagattccaa tcagtcctgg attgaggaca tctcttttgt  11100
acattcgtat gtcttaaccc ctgctcagct tgggggacta agtaaccttc aatactcaag  11160
```

-continued gctctacaca agaaacatcg gtgacccagg gactaccgct tttgcagagg tcaagagatt 11220
agaaactgtg ggttgctga gtccgagcat tatgacgaac agcttaacaa ggccacctgg 11280
caatggagat tgggccagtc tttgcaacga tccatactcc ttcaattttg agactgtcgc 11340
aagcccaaat attgtcctta agaaacatac acagaaagtc ttattcgaaa cttgttcaaa 11400
ccccttatta tccggagtac atacagagga taatgaggca gaagagaagg cattggctga 11460
attcttactc aatcaggaag tggttcaccc acgtgtcgcg catgctatca tggaggcaag 11520
ctctgtaggt aggagaaagc aaattcaagg gcttgttgac acaacaaaca ctgtgattaa 11580
gatcgcactg accaggaggc ctctcggcat caagagattg atgcggataa tcaattactc 11640
gagcatgcat gcgatgttat tcagagatga tgtttttttg cccaacagat ccaaccaccc 11700
cttagtctcc tctaatatgt gttcgctgac gctagcagat tatgcacgga acagaagctg 11760
gtcaccattg acagggggta ggaaaatact gggtgtgtct aatcccgata ccatagagct 11820
tgtagaaggg gagattctta gtgtcagcgg aggatgcgca aagtgtgaca gcggagatga 11880
acagtttacg tggttccatc tcccaggcaa tatagagctg actgatgaca ccaggaagaa 11940
ccccccgatg agagtaccat acctcggatc aaagactcag gagaggaggg ctgcctcgct 12000
tgcaaaaata gctcatatgt cacctcatgt gaaggcggca ttaagggcat catccgtgct 12060
aatctgggcg tacggggaca acgaagtgaa ctggactgcc gctcttcgga tcgcaaggtc 12120
tcggtgcaat ataagctcag agtatcttcg actattgtca cccctaccta cggctgggaa 12180
tctccaacat agattggacg atggcataac ccaaatgaca ttcacccctg catctctcta 12240
cagggtatca ccttacattc acatatccaa tgattctcaa aggctattta ccgaagaagg 12300
aatcaaagag gggaatgtgg tttaccaaca aattatgctc ttaggtttat ctctaattga 12360
atcactcttc ccaatgacga caactaagac atatgacgaa atcacattac acctccacag 12420
caaattcagc tgctgtatca gggaagcacc cgtcgcagta cccttcgagc tcctcgggtt 12480
ggcaccggaa ttaaggacag taaccacaaa taagttcatg tatgatccca gccctgtatc 12540
agagagagac tttgcgagac ttgacctggc tattttcaag agttacgagc ttaatctgga 12600
gtcgtactcc acaatggagt taatgaacat tctttcaata tctagtggga agttgattgg 12660
tgacaataca cgaaactgga tcagtgaggc ccaaaattca gatgtggtcc gcctattcga 12720
atatgcagca ctcgaagtgc ttctcgactg tgcttatcaa ctctactatc tgagggtgcg 12780
agggctaaat aacatcgtct tatacatgag tgatttatac aagaatatgc caggaattct 12840
actctccaat attgcggcca cgatatctca ccccatcatt cactcaaggt tgaatgcagt 12900
aggtctagtc aaccatgacg ggtcacatca acttgcagac acagatttca tcgaaatgtc 12960
tgcgaaactg ttagtctcct gcactagacg cgtgatctca agtctatacg cagggaataa 13020
gtatgatcta ctgtttccat ctgttttaga tgataacttg agtgagaaga tgcttcaact 13080
gatttcccgg ttatgttgtc tgtacacagt gctcttcgcc acaacaagag aaattccaaa 13140
aataagaggc ctatcggcgg aagaaaaatg ctcagtactc actgagtacc tattgtcaga 13200
tgctgtgaga ccattgcttg ggtccgaaca agtgagctct atcatgtctc ccaacataat 13260
tacgttccca gccaacctat attacatgtc taggaagagc cttaacttaa tcagagaacg 13320
agaggacaga gatatcatct tggcattatt gttccctcag gaaccgctac ttgagtttcg 13380
tccattacag gacatcggtg cgcgagtgaa agatcccttt actcgacaac ctgcagcatt 13440
catacgggag ttagacttga gtgctccagc aagatacgat gcatttacac ttgatgagtc 13500

-continued tcaccttgag cacacactgc cgaacccaga ggaagattac ttggtacgat acttgttcag 13560
aggaataggg actgcatctt cctcttggta taaggcatca catctacttt ctgtacctga 13620
ggtcagatgt gcaaggcatg gaagctcctt gtacctggcg gaaggaagtg gagctattat 13680
gagtcttctc gaactgcaca taccgcacga gactatctac tataatacgc ttttctcaaa 13740
tgagatgaac cccccacagc gacatttcgg accgactcca acacagtttt taaattcggt 13800
cgtttatagg aatctacagg cggaagtgcc atgtaaagat ggatttgtcc aggagtttcg 13860
tcccttatgg agagagaatg cagaagaaag tgacctgacc tcggataaag cagtaggata 13920
tatcacatct acggtgccat acaggactgt atcattactg cattgcgaca ttgaaattcc 13980
tccaggatcc aaccaaagct tactggatca actagctact aacttatccc tgattgccat 14040
gcactctgta agagagggcg gtgtcgtgat catcaaagta ctgtatgcaa tggggtacta 14100
cttccatcta ctcgtgaatt tattcactcc ctgttccaca aaaggatata ttctctctaa 14160
tggctatgct tgtagagggg atatggagtg ctacctgata ttcgtcatgg gctatgtggg 14220
cgggcccaca ttcgtacacg aagtggtgag aatggcaaag actctaatac agcagcacgg 14280
tacgctcctg tctaaatcgg acgaaattac gttgactggg ttatttacct cacagaagca 14340
tcgtgtaatg gacattctat ctagtccctt accgcgattg atgaaattct tgggggagaa 14400
cattgatgct gcgttgattg aagccggggg gcaacctgtc cgtccattct gtgcagagag 14460
tttagtaagc acgctaacag atatgactca gacgactcag atcattgcca gccacattga 14520
cacagtcatt cgatccgtga tctacatgga agccgagggt gaccttgctg acacagtatt 14580
cttatttact ccttacaatc tttctacaga cggtaaaaag agaacatcac ttaaacagtg 14640
cacaagacag attctagagg tcacaatact aggtctcaga gccaaagatc tcaataaagt 14700
gggtgatgta ataggcttaa tactcagagg tacagtttct ctggaggatc tcattccact 14760
gaggacatat ttgaagcgta gtacctgccc aaaatacttg aaggcagtcc tgggtattac 14820
taaactcaaa gaaatgttca cagacacttc tttattatac ctgactcgtg ctcagcaaaa 14880
attctatatg aaaaccatag gcaatgcggc caaggggtat tacagtaata atgatttcta 14940
aaggcaatca tatatgaata ggttctcttc ctagccaact gtatcctcat caacctggtc 15000
ataccatatt agaaaaaagt tgaatcccga ttctttggaa ctcgtattcg gattctaata 15060
attgtcttcg aacagaagta tacgtagttg tctttgacta tattcctgtc attcaccaaa 15120
tctttgtttg gt 15132

<210> SEQ ID NO 5
<211> LENGTH: 15186
<212> TYPE: DNA
<213> ORGANISM: Newcastle disease virus

<400> SEQUENCE: 5
accaaacaga gaatccgtga gttacgataa aaggcgaagg agcaattgaa gtcgcacggg 60
tagaaggtgt gaatctcgag tgcgagcccg aagcacaaac tcgagaaagc cttctgccaa 120
catgtcttcc gtatttgatg agtacgaaca gctcctcgcg gctcagactc gccccaatgg 180
agctcatgga gggggagaaa aagggagtac cttaaaagta gacgtcccgg tattcactct 240
taacagtgat gacccagaag atagatggag ctttgtggta ttctgcctcc ggattgctgt 300
tagcgaagat gccaacaaac cactcaggca aggtgctctc atatctcttt tatgctccca 360
ctcacaggta atgaggaacc atgttgccat tgcagggaaa cagaatgaag ccacattggc 420
cgtgcttgag attgatggct ttgccaacgg cacgccccag ttcaacaata ggagtggagt 480

-continued

```
gtctgaagag agagcacaga gatttgcgat gatagcagga tctctccctc gggcatgcag    540
caacggaacc ccgttcgtca cagccggggc agaagatgat gcaccagaag acatcaccga    600
taccctggag aggatcctct ctatccaggc tcaagtatgg gtcacagtag caaaagccat    660
gactgcgtat gagactgcag atgagtcgga aacaaggcga atcaataagt atatgcagca    720
aggcagggtc caaaagaaat acatcctcta ccccgtatgc aggagcacaa tccaactcac    780
gatcagacag tctcttgcag tccgcatctt tttggttagc gagctcaaga gaggccgcaa    840
cacggcaggt ggtacctcta cttattataa cctggtaggg gacgtagact catacatcag    900
gaataccggg cttactgcat tcttcttgac actcaagtac ggaatcaaca ccaagacatc    960
agcccttgca cttagtagcc tctcaggcga catccagaag atgaagcagc tcatgcgttt   1020
gtatcggatg aaaggagata atgcgccgta catgacatta cttggtgata gtgaccagat   1080
gagctttgcg cctgccgagt atgcacaact ttactccttt gccatgggta tggcatcagt   1140
cctagataaa ggtactggga aataccaatt tgccagggac tttatgagca catcattctg   1200
gagacttgga gtagagtacg ctcaggctca gggaagtagc attaacgagg atatggctgc   1260
cgagctaaag ctaaccccag cagcaatgaa gggcctggca gctgctgccc aacgggtctc   1320
cgacgatacc agcagcatat acatgcctac tcaacaagtc ggagtcctca ctgggcttag   1380
cgaggggggg tcccaagctc tacaaggcgg atcgaataga tcgcaagggc aaccagaagc   1440
cggggatggg gagacccaat tcctggatct gatgagagcg gtagcaaata gcatgaggga   1500
ggcgccaaac tctgcacagg gcactcccca atcggggcct cccccaactc ctgggccatc   1560
ccaagataac gacaccgact gggggtattg atggacaaaa cccagcctgc ttccacaaaa   1620
acatcccaat gccctcaccc gtagtcgacc cctcgatttg cggctctata tgaccacacc   1680
ctcaaacaaa catccccctc tttcctccct cccccctgctg tacaactccg cacgccctag   1740
ataccacagg cacaatgcgg ctcactaaca atcaaaacag agccgaggga attagaaaaa   1800
agtacgggta gaagagggat attcagagat cagggcaagt ctcccgagtc tctgctctct   1860
cctctacctg atagaccagg acaaacatgg ccacctttac agatgcagag atcgacgagc   1920
tatttgagac aagtggaact gtcattgaca acataattac agcccagggt aaaccagcag   1980
agactgttgg aaggagtgca atcccacaag gcaagaccaa ggtgctgagc gcagcatggg   2040
agaagcatgg gagcatccag ccaccggcca gtcaagacaa ccccgatcga caggacagat   2100
ctgacaaaca accatccaca cccgagcaaa cgaccccgca tgacagcccg ccggccacat   2160
ccgccgacca gccccccacc caggccacag acgaagccgt cgacacacag ttcaggaccg   2220
gagcaagcaa ctctctgctg ttgatgcttg acaagctcag caataaatcg tccaatgcta   2280
aaaagggccc atggtcgagc cccaagaggg ggaatcacca acgtccgact caacagcagg   2340
ggagtcaacc cagtcgcgga aacagtcagg aaagaccgca gaaccaagtc aaggccgccc   2400
ctggaaacca gggcacagac gtgaacacag catatcatgg acaatgggag gagtcacaac   2460
tatcagctgg tgcaacccct catgctctcc gatcaaggca gagccaagac aatacccttg   2520
tatctgcgga tcatgtccag ccacctgtag actttgtgca agcgatgatg tctatgatgg   2580
aggcgatatc acagagagta agtaaggttg actatcagct agatcttgtc ttgaaacaga   2640
catcctccat ccctatgatg cggtccgaaa tccaacagct gaaaacatct gttgcagtca   2700
tggaagccaa cttgggaatg atgaagattc tggatcccgg ttgtgccaac atttcatctc   2760
tgagtgatct acgggcagtt gcccgatctc acccggtttt agtttcaggc cctggagacc   2820
```

-continued

```
cctctcccta tgtgacacaa ggaggcgaaa tggcacttaa taaactttcg caaccagtgc   2880
cacatccatc tgaattgatt aaacccgcca ctgcatgcgg gcctgatata ggagtggaaa   2940
aggacactgt ccgtgcattg atcatgtcac gcccaatgca cccgagttct tcagccaagc   3000
tcctaagcaa gttagatgca gccgggtcga tcgaggaaat caggaaaatc aagcgccttg   3060
ctctaaatgg ctaattacta ctgccacacg tagcgggtcc ctgtccactc ggcatcacac   3120
ggaatctgca ccgagttccc ccccgcagac ccaaggtcca actctccaag cggcaatcct   3180
ctctcgcttc ctcagcccca ctgaatggtc gcgtaaccgt aattaatcta gctacattta   3240
agattaagaa aaaatacggg tagaattgga gtgccccaat tgtgccaaga tggactcatc   3300
taggacaatt gggctgtact ttgattctgc ccattcttct agcaacctgt tagcatttcc   3360
gatcgtccta caaggcacag gagatgggaa gaagcaaatc gccccgcaat ataggatcca   3420
gcgccttgac ttgtggactg atagtaagga ggactcagta ttcatcacca cctatggatt   3480
catctttcaa gttgggaatg aagaagccac tgtcggcatg atcgatgata aacccaagcg   3540
cgagttactt tccgctgcga tgctctgcct aggaagcgtc ccaaataccg gagaccttat   3600
tgagctggca agggcctgtc tcactatgat agtcacatgc aagaagagtg caactaatac   3660
tgagagaatg gttttctcag tagtgcaggc accccaagtg ctgcaaagct gtagggttgt   3720
ggcaaacaaa tactcatcag tgaatgcagt caagcacgtg aaagcgccag agaagattcc   3780
cgggagtgga accctagaat acaaggtgaa ctttgtctcc ttgactgtgg taccgaagaa   3840
ggatgtctac aagatcccag ctgcagtatt gaaggtttct ggctcgagtc tgtacaatct   3900
tgcgctcaat gtcactatta atgtggaggt agacccgagg agtcctttgg ttaaatcttt   3960
gtctaagtct gacagcggat actatgctaa cctcttcttg catattggac ttatgaccac   4020
cgtagatagg aaggggaaga aagtgacatt tgacaagctg gaaaagaaaa taaggagcct   4080
tgatctatct gtcgggctca gtgatgtgct cgggccttcc gtgttggtaa aagcaagagg   4140
tgcacggact aagcttttgg cacctttctt ctctagcagt gggacagcct gctatcccat   4200
agcaaatgct tctcctcagg tggccaagat actctggagt caaaccgcgt gcctgcggag   4260
cgttaaaatc attatccaag caggtaccca acgcgctgtc gcagtgaccg ccgaccacga   4320
ggttacctct actaagctgg agaaggggca cacccttgcc aaatacaatc cttttaagaa   4380
ataagctgcg tctctgagat tgcgctccgc ccactcaccc agatcatcat gacacaaaaa   4440
actaatctgt cttgattatt tacagttagt ttacctgtct atcaagttag aaaaaacacg   4500
ggtagaagat tctggatccc ggttggcgcc ctccaggtgc aagatgggct ccagaccttc   4560
taccaagaac ccagcaccta tgatgctgac tatccgggtt gcgctggtac tgagttgcat   4620
ctgtccggca aactccattg atggcaggcc tcttgcagct gcaggaattg tggttacagg   4680
agacaaagcc gtcaacatat acacctcatc ccagacagga tcaatcatag ttaagctcct   4740
cccgaatctg cccaaggata aggaggcatg tgcgaaagcc cccttggatg catacaacag   4800
gacattgacc actttgctca cccccccttgg tgactctatc cgtaggatac aagagtctgt   4860
gactacatct ggaggggggga gacaggggcg ccttataggc gccattattg gcggtgtggc   4920
tcttggggtt gcaactgccg cacaaataac agcggccgcg gctctgatac aagccaacca   4980
gaacgctgcc aacatcctcc ggcttaagga gagcattgct gcaaccaatg aagctgtaca   5040
tgaggtcact gacggattat cacaactagc ggtggcggtt gggaagatgc agcagtttgt   5100
taatgaccag tttaataata cggcgcgaga attggactgc ataaaaatta cacaacaggt   5160
tggtgtcgaa ctcaatttgt acctaacaga gttgactaca gtgttcgggc cacaaatcac   5220
```

-continued

```
ctcccctgct ttaactcagc tgaccatcca ggcactttat aatttagctg gtggcaatat   5280
ggattacttg ttgactaagt taggtgtagg gaacaatcaa ctcagctcgt taattggtag   5340
tggcttgatc accggcaacc ctatactata tgactcacag acccaactct tgggcataca   5400
ggtaaattta ccctcagtcg ggaacctaaa taatatgcgt gccacctact tggagacctt   5460
atccgtaagc acaaccaaag ggttcgcctc agcccttgtc ccgaaagttg tgacgcaagt   5520
cggttctgtg atagaagaac ttgatacctc atattgtata gaatccgatc tggatttata   5580
ttgcacaagg gtagtgacat tccccatgtc tcctggtatt tattcctgtc tgagcggcaa   5640
tacgtcagct tgtatgtatt caaagactga aggtgcactc actacaccat acatggccct   5700
caaaggctca gttattgcca attgcaagat gattacatgc agatgtgcag atcccccagg   5760
tatcatatcg caaaattacg ggaagctgt gtccctaata gataaacact catgcaatgt    5820
cttatcccta gacgggataa ccctgaggct cagtggggaa tttgatgcga cttatcaaaa   5880
gaacatctca atactagact ctcaagtcat cgtgacaggc aatctcgata tatcaactga   5940
gcttgggaat gtcaacaact cgataagcag tgccctggac aaattagcgg aaagcaacag   6000
caggctaaac aaagtcaatg tcaacctaac cagcacatct gctctcatta cttatattgt   6060
tttagctgtc atatctcttg ctttcggtgt aattagcctg gttctagcgt gctacctgat   6120
gtataaacaa aaagcacaac aaaagacctt actatggctt gggaacaata ccctcgatca   6180
gatgagagcc actacaagaa catgaataca gatgagagac gaatgtatcc ccagtagcaa   6240
ttcgtgcgtc aattctgata gcctgccaat tgggagaatt aagaaaaaac tactggatat   6300
aagtgaccaa agagcaatac acgggtagaa cggtcggaga agccacccct tagtcaggaa   6360
ccaggcttca caacatccgt tctaccgcat taccaatagc agacttcagt catggatcgt   6420
gtagttagca gagttgtact agagaacgaa gaaagagaag caaagaacac atggcgcttg   6480
gttttccgga tcgcagtctt atctctagta gtaatgactt tagctatctc tgtagccgcc   6540
ctggtataca gcatgggggc tagcacaccg agcgaccttg caggcatatc gacggtgatc   6600
tctaaggcag aggatagggt tacatcttta ctcagttcaa atcaagatgt ggtagatagg   6660
gtatataaac aggtggccct tgagtccccg ctggcgttgc taaatactga atctataatt   6720
atgaatgcaa taacttctct ctcttatcaa attaatgggg ctgcaaataa tagtgggtgt   6780
ggggcacctg ttcatgaccc agattatatt gggggggtag gcaaagaact catagtagat   6840
gacacaagtg atgtcacatc attctatcct tcagcatacc aagaacacct gaattttatc   6900
ccggcgccta ctacaggatc aggctgcact cggataccct cattcgacat gagcactacc   6960
cactattgtt atactcacaa tgtgatatta tctggttgca gagatcactc acactcacat   7020
cagtatttag cgctaggtgt acttcggaca tccgcaacag ggagggtatt cttttctact   7080
ctgcgttcca tcaatttaga tgacacccaa aatcggaagt cttgcagtgt gagtgcgact   7140
cctttaggtt gtgatatgct gtgctctaaa gtcatagaga ctgaggagga ggattataag   7200
tcaattaccc ccacatcaat ggtgcatgga aggttagggt ttgacggtca gtaccatgag   7260
aaggacttag acgtcacagt cttatttaag gattgggttg caaattaccc gggagtggga   7320
ggagggtctc ttattgacga ccgtgtatgg ttcccagttt atggagggct aaaacccaat   7380
tcgcctagcg acactgcaca agaagggaga tatgtaatat acaagcgcta taataacaca   7440
tgccccgatg gacaagatta ccaagttcgg atggctaagt cttcgtataa gcctggacgg   7500
tttggtagaa agcgcgtaca gcaagccatc ttatctatca aagtatcaac atctttgggc   7560
```

-continued

```
gaggacccgg tgctgactgt accgccaaat acagttacac tcatgggggc cgaaggcaga   7620
gtcctcacag tagggacatc tcatttcttg taccaacgag ggtcttcata cttctctccc   7680
gccttattat accctatgac agtacacaac aaaacagcta ctcttcatag tccttatata   7740
tttaatgctt tcactcggcc aggtagtgtc ccttgccagg catcagcaag gtgccctaac   7800
tcatgtatca ctggagtcta tactgatccg tatcctttag tcttccatag gaatcacacc   7860
ttgcgagggg tgttcgggac aatgcttgat aatgaacaag caaggttcaa ccccgtatct   7920
gcagtatttg attacacatc tcgcagtcgc ataacccggg taagttcaag cagcaccaag   7980
gcagcataca cgacatcgac atgttttaaa gttgtcaaga ccaataaagt ttattgcctt   8040
agcattgcag aaatatccaa caccctattt ggggaattca ggattgtccc tttactagtt   8100
gagatcctca aagatgacgg ggttagagaa gccaggtctg gctagttgag tcaattataa   8160
aggagttgga aagatggcat tgtatcacct atcttctgcg acatcaagaa tcaaaccgaa   8220
tgccggcgcg tgctcgaatt ccatgttgcc agttgaccac aatcagccag tgctcatgcg   8280
atcagattaa gccttgtcat taatctcttg attaagaaaa aatgtaagtg gcaatgagat   8340
acaaggcaaa acagctcatg gtaaataata cgggtaggac atggcgagct ccggtcctga   8400
aagggcagag catcagatta tcctaccaga gccacacctg tcttcaccat tggtcaagca   8460
caaactactc tattactgga aattaactgg gctaccgctt cctgatgaat gtgacttcga   8520
ccacctcatt ctcagccgac aatggaaaaa aatacttgaa tcggcctctc ctgatactga   8580
gagaatgata aaactcggaa gggcagtaca ccaaactctt aaccacaatt ccagaataac   8640
cggagtgctc caccccaggt gtttagaaca actggctaat attgaggtcc cagattcaac   8700
caacaaattt cggaagattg agaagaagat ccaaattcac aacacgagat atggagaact   8760
gttcacaagg ctgtgtacgc atatagagaa gaaactgctg gggtcatctt ggtctaacaa   8820
tgtcccccgg tcagaggagt tcagcagcat tcgtacggat ccggcattct ggtttcactc   8880
aaaatggtcc acagccaagt ttgcatggct ccatataaaa cagatccaga ggcatctgat   8940
ggtggcagct aagacaaggt ctgcggccaa caaattggtg atgctaaccc ataaggtagg   9000
ccaagtcttt gtcactcctg aacttgtcgt tgtgacgcat acgaatgaga acaagttcac   9060
atgtcttacc caggaacttg tattgatgta tgcagatatg atggagggca gagatatggt   9120
caacataata tcaaccacgg cggtgcatct cagaagctta tcagagaaaa ttgatgacat   9180
tttgcggtta atagacgctc tggcaaaaga cttgggtaat caagtctacg atgttgtatc   9240
actaatggag ggatttgcat acggagctgt ccagctactc gagccgtcag gtacatttgc   9300
aggagatttc ttcgcattca acctgcagga gcttaaagac attctaattg gcctcctccc   9360
caatgatata gcagaatccg tgactcatgc aatcgctact gtattctctg gtttagaaca   9420
gaatcaagca gctgagatgt tgtgtctgtt gcgtctgtgg ggtcacccac tgcttgagtc   9480
ccgtattgca gcaaaggcag tcaggagcca aatgtgcgca ccgaaaatgg tagactttga   9540
tatgatcctt caggtactgt ctttcttcaa gggaacaatc atcaacgggt acagaaagaa   9600
gaatgcaggt gtgtggccgc gagtcaaagt ggatacaata tatgggaagg tcattgggca   9660
actacatgca gattcagcag agatttcaca cgatatcatg ttgagagagt ataagagttt   9720
atctgcactt gaatttgagc catgtataga atatgaccct gtcaccaacc tgagcatgtt   9780
cctaaaagac aaggcaatcg cacaccccaa cgataattgg cttgcctcgt ttaggcggaa   9840
ccttctctcc gaagaccaga agaaacatgt aaaagaagca acttcgacta atcgcctctt   9900
gatagagttt ttagagtcaa atgattttga tccatataaa gagatggaat atctgacgac   9960
```

-continued

```
ccttgagtac cttagagatg acaatgtggc agtatcatac tcgctcaagg agaaggaagt  10020
gaaagttaat ggacggatct tcgctaagct gacaaagaag ttaaggaact gtcaggtgat  10080
ggcggaaggg atcctagccg atcagattgc acctttcttt cagggaaatg gagtcattca  10140
ggatagcata tccttgacca agagtatgct agcgatgagt caactgtctt ttaacagcaa  10200
taagaaacgt atcactgact gtaaagaaag agtatcttca aaccgcaatc atgatccgaa  10260
aagcaagaac cgtcggagag ttgcaacctt cataacaact gacctgcaaa agtactgtct  10320
taattggaga tatcagacaa tcaaattgtt cgctcatgcc atcaatcagt tgatgggcct  10380
acctcacttc ttcgaatgga ttcacctaag actgatggac actacgatgt tcgtaggaga  10440
ccctttcaat cctccaagtg accctactga ctgtgacctc tcaagagtcc ctaatgatga  10500
catatatatt gtcagtgcca gagggggtat cgaaggatta tgccagaagc tatggacaat  10560
gatctcaatt gctgcaatcc aacttgctgc agctagatcg cattgtcgtg ttgcctgtat  10620
ggtacagggt gataatcaag taatagcagt aacgagagag gtaagatcag acgactctcc  10680
ggagatggtg ttgacacagt tgcatcaagc cagtgataat ttcttcaagg aattaattca  10740
tgtcaatcat ttgattggcc ataatttgaa ggatcgtgaa accatcaggt cagacacatt  10800
cttcatatac agcaaacgaa tcttcaaaga tggagcaatc ctcagtcaag tcctcaaaaa  10860
ttcatctaaa ttagtgctag tgtcaggtga tctcagtgaa aacaccgtaa tgtcctgtgc  10920
caacattgcc tctactgtag cacggctatg cgagaacggg cttcccaaag acttctgtta  10980
ctatttaaac tatataatga gttgtgtgca gacatacttt gactctgagt tctccatcac  11040
caacaattcg caccccgatc ttaatcagtc gtggattgag gacatctctt ttgtgcactc  11100
atatgttctg actcctgccc aattaggggg actgagtaac cttcaatact caaggctcta  11160
cactagaaat atcggtgacc cggggactac tgcttttgca gagatcaagc gactagaagc  11220
agtgggatta ctgagtccta acattatgac taatatctta actaggccgc ctgggaatgg  11280
agattgggcc agtctgtgca acgacccata ctctttcaat tttgagactg ttgcaagccc  11340
aaatattgtt cttaagaaac atacgcaaag agtcctattt gaaacttgtt caaatccctt  11400
attgtctgga gtgcacacag aggataatga ggcagaagag aaggcattgg ctgaattctt  11460
gcttaatcaa gaggtgattc atccccgcgt tgcgcatgcc atcatggagg caagctctgt  11520
aggtaggaga aagcaaattc aagggcttgt tgacacaaca aacaccgtaa ttaagattgc  11580
gcttactagg aggccattag gcatcaagag gctgatgcgg atagtcaatt attctagcat  11640
gcatgcaatg ctgtttagag acgatgtttt ttcctccagt agatccaacc accccttagt  11700
ctcttctaat atgtgttctc tgacactggc agactatgca cggaatagaa gctggtcacc  11760
tttgacggga ggcaggaaaa tactgggtgt atctaatcct gatacgatag aactcgtaga  11820
gggtgagatt cttagtgtaa gcggagggtg tacaagatgt gacagcggag atgaacaatt  11880
tacttggttc catcttccaa gcaatataga attgaccgat gacaccagca agaatcctcc  11940
gatgagggta ccatatctcg ggtcaaagac acaggagagg agagctgcct cacttgcaaa  12000
aatagctcat atgtcgccac atgtaaaggc tgccctaagg gcatcatccg tgttgatctg  12060
ggcttatggg gataatgaag taaattggac tgctgctctt acgattgcaa aatctcggtg  12120
taatgtaaac ttagagtatc ttcggttact gtcccctttta cccacggctg ggaatcttca  12180
acatagacta gatgatggta taactcagat gacattcacc cctgcatctc tctacaggtg  12240
tcaccttaca ttcacatatc caatgattct caaaggctgt tcactgaaga aggagtcaaa  12300
```

-continued

```
gaggggaatg tggtttacca acagagtcat gctcttgggt ttatctctaa tcgaatcgat  12360
ctttccaatg acaacaacca ggacatatga tgagatcaca ctgcacctac atagtaaatt  12420
tagttgctgt atcagagaag cacctgttgc ggttcctttc gagctacttg gggtggtacc  12480
ggaactgagg acagtgacct caaataagtt tatgtatgat cctagccctg tatcggaggg  12540
agactttgcg agacttgact tagctatctt caagagttat gagcttaatc tggagtcata  12600
tcccacgata gagctaatga acattctttc aatatccagc gggaagttga ttggccagtc  12660
tgtggtttct tatgatgaag atacctccat aaagaatgac gccataatag tgtatgacaa  12720
tacccgaaat tggatcagtg aagctcagaa ttcagatgtg gtccgcctat ttgaatatgc  12780
agcacttgaa gtgctcctcg actgttctta ccaactctat tacctgagag taagaggcct  12840
agacaatatt gtcttatata tgggtgattt atacaagaat atgccaggaa ttctactttc  12900
caacattgca gctacaatat ctcatcccgt cattcattca aggttacatg cagtgggcct  12960
ggtcaaccat gacggatcac accaacttgc agatacggat tttatcgaaa tgtctgcaaa  13020
actattagta tcttgcaccc gacgtgtgat ctccggctta tattcaggaa ataagtatga  13080
tctgctgttc ccatctgtct tagatgataa cctgaatgag aagatgcttc agctgatatc  13140
ccggttatgc tgtctgtaca cggtactctt tgctacaaca agagaaatcc cgaaaataag  13200
aggcttaact gcagaagaga aatgttcaat actcactgag tatttactgt cggatgctgt  13260
gaaaccatta cttagccccg atcaagtgag ctctatcatg tctcctaaca taattacatt  13320
cccagctaat ctgtactaca tgtctcggaa gagcctcaat ttgatcaggg aaagggagga  13380
cagggatact atcctggcgt tgttgttccc ccaagagcca ttattagagt tcccttctgt  13440
gcaagatatt ggtgctcgag tgaaagatcc attcacccga caacctgcgg catttttgca  13500
agagttagat ttgagtgctc cagcaaggta tgacgcattc acacttagtc agattcatcc  13560
tgaactcaca tctccaaatc cggaggaaga ctacttagta cgatacttgt tcagagggat  13620
agggactgca tcttcctctt ggtataaggc atctcatctc ctttctgtac ccgaggtaag  13680
atgtgcaaga cacgggaact ccttatactt agctgaaggg agcggagcca tcatgagtct  13740
tctcgaactg catgtaccac atgaaactat ctattacaat acgctctttt caaatgagat  13800
gaaccccccg caacgacatt tcgggccgac ccccaactcag tttttgaatt cggttgttta  13860
taggaatcta caggcggagg taacatgcaa agatggattt gtccaagagt tccgtccatt  13920
atggagagaa aatacagagg aaagtgacct gacctcagat aaagcagtgg ggtatattac  13980
atctgcagtg ccctacagat ctgtatcatt gctgcattgt gacattgaaa ttcctccagg  14040
gtccaatcaa agcttactag atcaactagc tatcaattta tctctgattg ccatgcattc  14100
tgtaagggag ggcggggtag taatcatcaa agtgttgtat gcaatgggat actactttca  14160
tctactcatg aacttgtttg ctccgtgttc cacaaaagga tatattctct ctaatggtta  14220
tgcatgtcga ggagatatgg agtgttacct ggtatttgtc atgggttacc tgggcgggcc  14280
tacatttgta catgaggtgg tgaggatggc aaaaactctg gtgcagcggc acggtacgct  14340
cttgtctaaa tcagatgaga tcacactgac caggttattc acctcacagc ggcagcgtgt  14400
gacagacatc ctatccagtc ctttaccaag attaataaag tacttgagga agaatattga  14460
cactgcgctg attgaagccg ggggacagcc cgtccgtcca ttctgtgcgg agagtctggt  14520
gagcacgcta gcgaacataa ctcagataac ccagattatc gctagtcaca ttgacacagt  14580
tatccggtct gtgatatata tggaagctga gggtgatctc gctgacacag tatttctatt  14640
taccccttac aatctctcta ctgacgggaa aaagaggaca tcacttatac agtgcacgag  14700
```

-continued

```
acagatccta gaggttacaa tactaggtct tagagtcgaa aatctcaata aaataggcga  14760

tataatcagc ctagtgctta aaggcatgat ctccatggag gaccttatcc cactaaggac  14820

atacttgaag catagtacct gccctaaata tttgaaggct gtcctaggta ttaccaaact  14880

caaagaaatg tttacagaca cttctgtatt gtacttgact cgtgctcaac aaaaattcta  14940

catgaaaact ataggcaatg cagtcaaagg atattacagt aactgtgact cttaacgaaa  15000

atcacatatt aataggctcc ttttttggcc aattgtattc ttgttgattt aatcatatta  15060

tgttagaaaa aagttgaacc ctgactcctt aggactcgaa ttcgaactca aataaatgtc  15120

ttaaaaaaag gttgcgcaca attattcttg agtgtagtct cgtcattcac caaatctttg  15180

tttggt                                                            15186
```

NEWCASTLE DISEASE VIRUS AND THE USE THEREOF AS A VACCINE

CROSS-REFERENCE TO RELATED APPLICATION

This application is a Section 371 of International Application No. PCT/MX2011/000141,filed Nov. 18, 2011, which was published in the Spanish language on May 24, 2012 under International Publication No. WO 2012/067483 A3, and the disclosure of which is incorporated herein by reference.

TECHNICAL FIELD OF THE INVENTION

The present invention relates to a Newcastle disease virus and, more specifically to viral strains constructed by reverse genetics and recombination for use in the preparation of homologous vaccines permitting a viral load reduction either as live virus vaccines or emulsion vaccine, alone or combined with other viral agents.

BACKGROUND

The Newcastle disease virus (NDV) belongs to serotype 1 of avian paramyxovirus belonging to the genus *Avulavirus* of the family Paramyxoviridae (Mayo, 2002). This disease is considered one of the pathological processes with greater economic impact on the poultry industry. The virus is capable to affect respiratory, digestive and nervous systems. Digestive tract secretions are a major source of infection for virus replication. The Newcastle disease virus is transmitted during the incubation period that lasts 4 to 6 days and for a limited period of time during convalescence. The severity of the disease symptoms depends on the genotype, strain, dose, immune status of the bird, exposition route, the presence of other infectious agents and environmental conditions. In acute cases, the only clinical manifestation of the disease is mortality.

To date, the presence of this disease is of great concern although there is no evidence of significant mortality problems probably because of the protection offered by vaccination. However, vaccination does not prevent viral shedding and dissemination.

It is essential to determine the pathogenicity of a strain based on its biological behavior and genetic structure.

According to its pathogenicity, the Newcastle disease virus is classified into three types: a) lentogenic, presenting low pathogenicity, b) mesogenic, presenting moderate pathogenicity, and c) velogenic, presenting high pathogenicity. At genetic level, the pathogenicity is mainly determined by the amino acid sequence present at the cleavage site of the fusion protein of the Newcastle virus, specifically the 5 amino acids before the cleavage site. Greater the number of basic amino acids, greater is the degree of pathogenicity. Thus, the velogenic phenotype corresponds to the presence of 4 basic amino acids while the lentogenic phenotype corresponds to the presence of two basic amino acids at the cleavage site. (Glickman et al. 1988; Peeters B., et al. 1999).

Six encoded proteins participating in the infection and replication are found in the virus genome: 1) a nucleoprotein (NP), the phosphoprotein, (P), the matrix protein (M), the fusion protein (F), an hemagglutinin-neuraminidase (HN) and an RNA-dependent RNA polymerase (L) (de Leeuw and Peeters, 1999).

Among the proteins encoded in the virus genome, two are the most important from an antigenic point of view: hemagglutinin-neuraminidase (HN) and the fusion protein (F). These two proteins found on the surface of the viral envelope are the target of the humoral immune response.

The function of the fusion protein is to perform the cell entry process of the viral particle. This protein is the main responsible for the pathogenicity phenotype. This phenomenon depends on the chemical properties of the amino acids present at the cleavage side of the protein. The predominance of basic amino acids expresses a velogenic phenotype, while their low presence characterizes lentogenic strains (Glickman et al. 1998).

The encoding gene for the HN protein is responsible for the activities related to hemagglutination and neuraminidase. Its main function is to promote cell binding, and the breaking of sialic acid chains, respectively. Immunologically, it is the most important of all the proteins of this virus because it is the most antigenic. The encoding gene for the protein responsible for the transcription of the viral genes and the replication (Cobaleda et al., 2002).

Studies conducted in the year 2000 by Dr. Swayne and Dr. Suarez showed that there are differences regarding the capacity to neutralize virus replication at respiratory tract level depending on the homology level existing between the vaccine virus and the challenge virus in a study performed with various high pathogenicity viruses. The presence of antigenic and genetic diversity with regard to Newcastle disease virus has been recognized and it is known that any strain can protect against the mortality caused by a challenge from another lineage but however epidemiological outbreaks continue to appear.

In studies conducted by Pedersen J C et al. (J. Clin Microbiol 2004, 42:2329-2334), it was shown by phylogenetic analyses that the viruses isolated in California, Nevada and Texas were related to viruses isolated in Mexico and Central America, that are sequentially remote from the La Sota strain isolated in 1946 in the United States of America, the strain used in most commercial vaccines.

Commercial vaccines are prepared using a lentogenic strain and are marketed as live virus and inactivated virus, being the La Sota strain of the Newscastle disease virus the most used worldwide, among others. This strain belongs to the genotype II, according to the classification proposed by Czegledi et al. in 2006.

Miller et al., 2007 (Vaccine 2007, 25: 7238-7246) report that the homologous vaccination with the challenge reduces virus elimination compared to the reduction observed in vaccines prepared with heterologous strains, facilitating viral circulation and therefore increasing the possibility of mutations, confirming thus the need to effectively reduce viral shedding for a better control of the disease.

Several technologies have been proposed to tackle these problems, for example, US application 2010/0183664 offers the use of nucleotides sequence encoding for NP, P, M and L proteins of a low pathogenicity virus and for F and HN proteins from a high pathogenicity virus from genotype VII, however it is considered that said vaccine may result in the emergence of new virus strains, and thus it is not appropriate for use as live vaccine.

U.S. Pat. No. 7,442,379 proposes the use of an RNA molecule comprising specific binding sites for a NCD virus polymerase and a mutation in the signals required to inhibit replication and transcription of a NCD virus linked to a RNA sequence derived from heterologous viruses such as the human immunodeficiency virus, Marek's disease, influenza, etc.

However, current vaccines are considered as a factor in the outbreak of diseases because there is no appropriately control of elimination of the virus, being necessary vaccination that should not only prevent mortality but also reduce viral shedding and eliminate or prevent mutations, i.e. it is necessary to have highly antigenic fragment vaccines.

Sequences List.

SEQ ID NO 1 corresponds to sequence fragment of the genome of the Newcastle disease virus encoding for F and HN proteins designed by phylogenetic analysis and identified as SEQ 1.

SEQ 2 corresponds to sequence of the Newcastle disease virus identified as APMV1/Chicken/Mexico/RecP05/2005 designed by phylogenetic analysis of strain APMV1/Chicken/Mexico/P05/2005 identified as SEQ 2.

SEQ 3 corresponds to sequence of the Newcastle disease virus identified as 1083 (Fontana)/72/RecP05 designed by phylogenetic analysis of strain 1083 (Fontana)/72 identified as SEQ 3

SEQ 4 corresponds to sequence of the Newcastle disease virus identified as Gamefowl/U.S.(CA)/211472/02/RecP05 designed by phylogenetic analysis of strain Gamefowl/U.S.(CA)/211472/02 identified as SEQ 4

SEQ 5 corresponds to sequence of the Newcastle disease virus identified as RecLSP05 designed by phylogenetic analysis of strain LaSota identified as SEQ 5.

DETAILED DESCRIPTION OF THE INVENTION

The present invention consists of several Newcastle disease viruses constructed through reverse genetics and molecular biology techniques, fragments of the sequences encoding for F and HN proteins of said Newcastle disease viruses, plasmids containing sequences encoding for one or more of NP, P, M, F, HN and L proteins of Newcastle disease virus that are useful for making live or emulsion vaccines and for being used as vectors for incorporating the proteins of other types of heterologous viruses.

The invention is characterized because sequences encoding for the highly antigenic F and HN proteins have been designed offering thus a better prevention of the Newcastle disease through the reduction of viral shedding.

The genome of the antigenic sequences of F and HN proteins of the Newcastle disease virus of the present invention was obtained through a phylogenetic analysis with the whole genome of two or more varieties of Newcastle disease viruses isolated from strains from the region of interest, or from others considered appropriate, showing various degrees of pathogenicity, preferably high pathogenicity, because they are responsible for major economic losses to poultry industry, although low pathogenicity strains also cause epidemic outbreaks, in order to identify highly antigenic sequences offering the best properties to the vaccines made with them.

Sequence alignment was done using commercial programs such as "MegaAlign" of "DNA star"; and "PrimerPremier" of "PremierBiosoft". Various fragment sequences corresponding to the F and HN proteins were designed and tests were conducted to determine the most antigenic ones through immunogenicity tests in chicken free from specific pathogens, determining that SQ1 sequence offered the best results.

Then, several sequences of the fragments encoding for NP, P, M, and L proteins were designed through the phylogenic analysis of the viruses observed in field outbreaks, the sequence alignment was done using commercial programs such as MegaAlign" of "DNA star"; and "PrimerPremier" of "PremierBiosoft".

To obtain the complete sequence of viruses of the present invention, two to five fragments containing the sequences encoding for NP, P, M, F, HN and L proteins were constructed for cloning into a plasmid in order to facilitate manipulation and assembly.

To amplify the cDNA of the virus genome, various primers were designed with corresponding hybridization sites between 3.5 and 5.5 Kb.

To amplify the genome of the designed viruses, a kit was used such as "SuperScript™ One-Step RT-PCR for Long Templates", that contains an enzyme mix providing greater fidelity and processivity in the amplified DNA fragments. The amplification of the viral genome is performed according to the following conditions:

Amplification Reaction Mix:

| Component | (volume) | (Final concentration) |
|---|---|---|
| Premixed 2X Buffer | 25 µl | 1X |
| RNA mold | 1-5 µl | 10 pg-1 µg |
| Forward Oligonucleotide (10 µM) | 1 µl | 0.2-0.4 µM |
| Reverse Oligonucleotide (10 µM) | 1 µl | 0.2-0.4 µM |
| RT/Platinum ® Taq HiFi | 1-2 µl | 1 Unit |
| Water q.s. | 50 µl | |
| Thermocycler Amplification conditions: | | |
| Retrotranscripction | | |
| Amplification | 45° C. | 30 min |
| PCR | | |
| Denaturation | 94° C. | 2 min |
| 30 cycles of: | | |
| Denaturation | 94° C. | 45 s |
| Hybridization | 50° C. | 1 min |
| Polimerization | 68° C. | 1 min/kb |
| After 30 cycles: | | |
| Polimerization | 72° C. | 10 min |

Then, the plasmids were assembled in order to complete the whole genome of the viruses as cDNA.

The viruses of the present invention correspond preferably to the sequences shown in Sequences 2 to 5 and identified as SEQ 2, SEQ 3, SEQ 4 and SEQ 5 incorporating the highly antigenic fragment sequence of the genome of the Newcastle disease virus encoding for F and HN proteins as shown in the SEQ 1.

In one of preferred embodiments of the present invention, the sequences identified as SEQ 2, SEQ 3, SEQ 4 and SEQ 5 are obtained by adding 4 segments in a suitable plasmid such as pCR XL TOPO, following the protocols described by the manufacturer of said plasmid, that are then assembled through techniques well known for skilled people in the technical field.

The recovery of the recombinant Newcastle disease viruses can be performed preferably in Hep-2 cells, which is a cell line derived from a human tracheal tumor tissue, the recovery is accomplished by the method previously reported by Peeters et al. in 1999, as follows:

Six-well cell culture plates containing Hep-2 cells of approximately 24 hours in monolayer at 70-80% confluence are used. Each well is infected with the MVS/T7 Ankara virus (Fuerst et al., 1987) at a cell:virus ratio of 1:1.

Subsequently, the cells are transfected using lipofectamine as recommended by the supplier with 1, 0.8, 0.8 y 0.8 µgs of each one of four plasmids formed.

The transfection is incubated at 37° C. during 72 hours. Subsequently cell culture and supernatant are harvested, and then used for infecting specific-pathogen-free chicken embryos. The embryos are incubated during 72-96 hours at 37° C. and then the allantoic fluid is harvested.

In order to identify allantoic fluid samples positive for Newcastle disease virus, an hemagglutination essay is performed with red blood cells of chicken embryo according to the method reported by Alexander in 2009. The positive samples are subjected to neutralization with antibodies anti Newcastle disease virus to ensure that the hemagglutination (HA) is due to the HN protein of the Newcastle disease virus. For this purpose 50 μl of allantoic fluid and 50 μl of Newcastle disease virus antiserum are mixed, then 50 μl of 1% chicken red blood cells are added. The samples losing their hemagglutinating capacity by neutralization with anti Newcastle disease virus antibodies, known as hemaglutination Inhibition (HI), are considered positive for Newcastle disease virus.

One of the samples positive for both tests (HA and HI) was selected to be subjected to 5 to 10 serial passages in specific-pathogen-free chicken embryos. Subsequently, each of the samples of each passage in embryo was sequenced in the cleavage site region of the F protein of the Newcastle disease virus in order to identify the lentogenic genotype and its stability in the effected passages.

Another of the preferred ways of obtaining the viruses of the present invention is by modifying the viral strains of the Newcastle disease or isolating them from new or known high pathogenicity field outbreaks, preferably virulent and generating high levels of mortality in poultry, incorporating the sequences encoding for F and HN proteins of the present invention preferably contained in a plasmid.

The viruses obtained in the present invention are used for preparing emulsion or lyophilized vaccines.

For preparing emulsion vaccines, the Newcastle disease viruses of the present invention are primarily inactivated by commonly used methods with chemical agents such as phormol, binary bromomethylamine or beta-propiolactone in concentration not exceeding the limits allowed by health regulation. Subsequently, the inactivated viruses are mixed in a tank with an oily adjuvant, such as mineral oil, and one or more surfactants agents in appropriate proportions.

The preparation of lyophilized vaccines containing the recombinant strains of the present invention is performed using a stabilizer that may be based on skimmed milk, saccharose or that may be of any other type, in a proportion of 40/50% virus and 50-60% stabilizing agent; the components are mixed and placed in glass containers in volumes ranging from 3.5 to 4 ml per vial, the lids are placed and they are introduced in the lyophilizer according to a previously set program for controlling the lyofilization parameters as follows:

| Segment | Ramp | Hold | Time |
|---|---|---|---|
| 1 | 0.2 C./min. | −40 C. | 3 hr |
| 2 | 0.10 C./min. | −20 C. | 2 hr |
| 3 | 0.1 C./min. | −5 C. | 1 hr |
| 4 | 0.05 C./min | 10 C. | 1 hr |
| 5 | 0.1 C./min | 27 C. | 0.5 h |

In another preferred embodiment of the present invention, the sequences identified as SEQ 2, SEQ 3, SEQ 4 and SEQ 5 are also used as vectors to incorporate sequences or fragments of heterologous viruses such as proteins of influenza virus, Marek's disease, etc.

The description of the present invention will be further illustrated by the following examples that should not be considered limiting.

EXAMPLE 1

A lentogenic virus of the highly antigenic genotype V was constructed, denominated APMV1/Chicken/Mexico/RecP05/2005 according to the sequence identified as SEQ 2 through a phylogenetic analysis where preference was given to the sequence of a virus isolated from infected farms field. Four fragments of said sequence were constructed and amplified and then cloned into the pCR XL TOPO plasmid, according to the protocols described by the manufacturer, obtaining the corresponding plasmids. Said plasmids were then assembled to complete the entire genome of the virus as cDNA.

EXAMPLE 2

Plasmids containing the genome sequences encoding for NP, P, M and L proteins of two strains of Newcastle disease virus, 1083 (Fontana)/72 virus and Gamefowl/U.S.(CA)/211472/02 virus were prepared, with sequence modification by a plasmid containing the genome sequence encoding for F and HN proteins of SEQ 1 according to the procedure described herein for amplification, resulting in a new highly antigenic viruses identified as 1083 (Fontana)/72/RecP05 and Gamefowl/U.S.(CA)/211472/02/RecP05 the complete sequences of which correspond to the sequences described in SEQ 3 and SEQ 4.

EXAMPLE 3

Plasmids containing the genome sequences encoding for NP, P, M and L proteins of a Newcastle disease strain belonging to genotype II were prepared, corresponding to the virus known as LaSota, that were assembled with a plasmid containing the genome sequence encoding for F and HN proteins of SEQ 1, according to the procedure described herein for amplification, resulting in a new virus identified as RecLSP05 the sequence of which corresponds to the sequence described in SEQ 5.

EXAMPLE 4

An emulsion vaccine was prepared containing the APMV1/Chicken/Mexico/RecP05/2005 strain prepared in example 1. For such purpose, the APMV1/Chicken/Mexico/RecP05/2005 virus was first inactivated by commonly used methods with chemical agents such as phormol, binary bromomethylamine or beta-propiolactone at appropriate concentrations. Once inactivated, the APMV1/Chicken/Mexico/RecP05/2005 virus was incorporated in a proportion of 20% in a tank in which an oily agent, such as mineral oil, has previously been placed in a proportion of 70% and the surfactants TWEEN 80 (e.g. polysorbate) and SPAN 80, (e.g. sorbitan), while stirring the emulsion between 6 and 8 hours. Once the emulsion was formed, it was packaged and the samples were shipped for quality control testing.

EXAMPLE 5

A lyophilized live vaccine containing the APMV1/Chicken/Mexico/RecP05/2005 strain of example 1 as antigen was prepared. For such purpose, a stabilizer was used, that may be based on skimmed milk or saccharose or that may be of any other type, in a proportion of 40/50% antigen and 50-60% stabilizing agent; the components are mixed and placed in glass containers in volumes ranging from 3.5 to 4 ml per vial, the lids are placed and they are introduced in the lyophilizer.

The lyophilizer was programmed as follows:

| SEGMENT | RAMP | HOLD | TIME |
|---|---|---|---|
| 1 | 0.2 C./min. | −40 C. | 3 hr |
| 2 | 0.10 C./min. | −20 C. | 2 hr |
| 3 | 0.1 C./min. | −5 C. | 1 hr |
| 4 | 0.05 C./min | 10 C. | 1 hr |
| 5 | 0.1 C./min | 27 C. | 0.5 h |

Having set the parameters, the lyophilization process was initiated.

After lyophilization, remove the vials, place the aluminum lid and ship the vials requested for quality control testing according to already known procedures.

EXAMPLE 6

The live and emulsion vaccines formulated with the APMV1/Chicken/Mexico/RecP05/2005 virus strain, prepared according to the procedure described in examples 4 and 5, were used in a test of immunogenicity in broilers. The test was performed by applying 0.03 ml of the vaccine containing $10^8$ DIE/ml live virus of the APMV1/Chicken/Mexico/RecP05/2005 antigenic strain by ocular route to two groups of 3-week old broilers. One week after the application of the virus, a group of chicks received a dose of 0.5 ml of the emulsion vaccine, a group remaining without treatment. The birds were housed in Horsfall Bauer units, under isolation conditions.

TABLE 6.1

Experimental Design

| Group | Treatment received | No. of birds | Dose |
|---|---|---|---|
| A | Live vaccine | 10 | 0.03 |
| B | Live + Emulsion vaccine | 10 | 0.03 |
| C | Control | 10 | N/A |

The birds were bled every week for antibody determination by hemagglutination Inhibition (HI) for LaSota, APMV1/Chicken/Mexico/P05/2005 and APMV1/Chicken/Mexico/RecP05/2005 antigens.

Newcastle disease virus APMV1/Chicken/Mexico/P05/2005 was used as challenge strain at a concentration of 200,000 DIE per each 0.2 ml 4 weeks post-vaccination.

The evaluated parameters were: HI response 4 weeks post-vaccination, protection against challenge and quantity of viral particles in tracheal and cloacal swabs, 3 and 7 days post-challenge.

Samples of oropharyngeal and cloacal exudate were collected with wooden swabs 3 and 7 days post-challenge for rt-PCR testing. Likewise, trachea, spleen and lung from the births culled at the end of the test were collected.

TABLE 6.2

Geometric mean (GM) of antibody determination essays by HI of La Sota strain of the Newcastle disease virus.

| Group | Bleeding 0 | Bleeding 1 | Bleeding 2 | Bleeding 3 | Bleeding 4 |
|---|---|---|---|---|---|
| A | 49 | 10 | 20 | 14 | 22 |
| B | — | 10 | 28 | 368 | 435 |
| C | — | 13 | 10 | 12 | 19 |

* For the initial bleeding, only 10 animals were bled out of a total of 40.

TABLE 6.3

Geometrical mean (GM) of antibodies determination essays by HI of APMV1/Chicken/Mexico/P05/2005 strain of the Newcastle disease virus.

| Group | Bleeding 0 | Bleeding 1 | Bleeding 2 | Bleeding 3 | Bleeding 4 |
|---|---|---|---|---|---|
| A | 25 | 10 | 11 | 11 | 11 |
| B | — | 10 | 14 | 121 | 173 |
| C | — | 10 | 10 | 11 | 12 |

* For the initial bleeding, only 10 animals were bled out of a total of 40.

TABLE 6.4

Geometrical mean (GM) of antibodies determination essays by HI of APMV1/Chicken/Mexico/RecP05/2005 strain of the Newcastle disease virus.

| Group | Bleeding 0 | Bleeding 1 | Bleeding 2 | Bleeding 3 | Bleeding 4 |
|---|---|---|---|---|---|
| A | 35 | 10 | 14 | 12 | 14 |
| B | — | 10 | 16 | 226 | 296 |
| C | — | 11 | 10 | 11 | 15 |

* For the initial bleeding, only 10 animals were bled out of a total of 40.

TABLE 6.5

Mortality after challenge with APMV1/Chicken/Mexico/P05/2005 strain.

| Group | No of birds | No of dead birds | Percentage |
|---|---|---|---|
| A | 9* | 0 | 0% |
| B | 9* | 0 | 0% |
| C | 10** | 10 | 100 |

*One bird died from causes not related to the challenge.
**The animals died between 4 and 5 day post-challenge.

TABLE 6.6

Shows individually the viral particle titers of APMV1/Chicken/Mexico/P05/2005 strain of the Newcastle disease virus detected by rt-PCR 3 days post-challenge (dpd) in tracheal swabs.

| Chikcken No | Group A | Group B | Group C |
|---|---|---|---|
| 1 | Negative | Negative | Negative |
| 2 | Negative | Negative | $4.18 \times 10^6$ |
| 3 | Negative | Negative | Negative |
| 4 | Negative | Negative | Negative |
| 5 | $6.06 \times 10^6$ | Negative | $3.3 \times 10^6$ |
| 6 | $1.33 \times 10^6$ | Negative | Negative |
| 7 | Negative | Negative | $2.82 \times 10^7$ |
| 8 | Negative | Negative | $1.82 \times 10^6$ |
| 9 | Negative | Negative | $1.55 \times 10^7$ |
| 10 | Negative | Negative | $2.66 \times 10^7$ |
| mg | $10^{1.3}$ | 0 | $10^{4.15}$ |
| Difference | 2.85 | 4.15 | 0 |

TABLE 6.7

| Shows individually the viral particles titers of APMV1/Chicken/Mexico/P05/2005 strain of the Newcastle disease virus, detected by rt-PCR 3 days post-challenge (dpc) in cloacal swabs. | | | |
|---|---|---|---|
| Chicken No | Group A | Group B | Group C |
| 1 | Negative | Negative | Negative |
| 2 | Negative | Negative | $4.18 \times 10^6$ |
| 3 | Negative | Negative | Negative |
| 4 | Negative | Negative | Negative |
| 5 | $6.06 \times 10^6$ | Negative | $3.3 \times 10^6$ |
| 6 | $1.33 \times 10^6$ | Negative | Negative |
| 7 | Negative | Negative | $2.82 \times 10^7$ |
| 8 | Negative | Negative | $1.82 \times 10^6$ |
| 9 | Negative | Negative | $1.55 \times 10^7$ |
| 10 | Negative | Negative | $2.66 \times 10^7$ |
| mg | $10^{1.3}$ | 0 | $10^{4.15}$ |
| Difference | 2.85 | 4.15 | 0 |

TABLE 6.8

| Shows individually the viral particle titers of APMV1/Chicken/Mexico/P05/2005 strain of the Newcastle disease virus detected by rt-PCR 7 days post-challenge (dpc) in tracheal swabs. | | | |
|---|---|---|---|
| Chicken No | Group A | Group B | Group C |
| 1 | $6.02 \times 10^5$ | Negative | NA |
| 2 | Negative | Negative | NA |
| 3 | Negative | Negative | NA |
| 4 | $6.36 \times 10^5$ | Negative | NA |
| 5 | Negative | Negative | NA |
| 6 | Negative | Negative | NA |
| 7 | $1.12 \times 10^6$ | Negative | Negative |
| 8 | $8.18 \times 10^5$ | Negative | Negative |
| 9 | Negative | Negative | Negative |
| 10 | Negative | Negative | Negative |
| MG | 2 . . . 35 | 0 | 0 |

TABLE 6.9

| Shows individually the viral particle titers of APMV1/Chicken/Mexico/P05/2005 strain of the Newcastle disease virus, detected by rt-PCR 7 days post-challenge (dpc) in cloacal swabs. | | | |
|---|---|---|---|
| Chicken No | Group A | Group B | Group C |
| 1 | Negative | Negative | NA |
| 2 | Negative | Negative | NA |
| 3 | Negative | Negative | NA |
| 4 | $3.4 \times 10^6$ | Negative | NA |
| 5 | $1.13 \times 10^6$ | Negative | NA |
| 6 | Negative | Negative | NA |
| 7 | Negative | Negative | Negative |
| 8 | Negative | Negative | Negative |
| 9 | Negative | Negative | Negative |
| 10 | Negative | Negative | Negative |
| MG | 1.26 | 0 | 0 |

Necropsies: All the lesions of the birds dead post-challenge were diagnosed by the pathologist as related to the viral infection. The surviving control animals culled at the end of the test showed lesions characteristic of Newcastle disease.

From the above results, it derives that the antibodies response to the homologous strain in the group vaccinated with live virus was low, showing titers of 11 and 14 for APMV1/Chicken/Mexico/P05/2005 and APMV1/Chicken/Mexico/RecP05/2005 antigens, respectively, quality control specification setting a titer of 32 on Week 4 post-vaccination. In this sense, the group vaccinated with live virus and the emulsion vaccine 70/30 meet this condition, the geometric mean reached with APMV1/Chicken/Mexico/P05/2005 antigen was 173, while the geometric mean reached with APMV1/Chicken/Mexico/RecP05/2005 antigen was 296. Although the HI titers for the APMV1/Chicken/Mexico/P05/2005 and APMV1/Chicken/Mexico/RecP05/2005 strains were low in the group vaccinated only with live virus, viral shedding in the tracheal swab on Day 3 post-challenge compared to the control group was lower by up to log 3, while in the case of the cloacal swab, it was lower by 2.85.

Live vaccines in combination with experimental emulsion vaccine prepared with the APMV1/Chicken/Mexico/RecP05/2005 strain of the Newcastle disease virus offer protection and reduction of viral shedding to 0 after challenge with a homologous virus.

EXAMPLE 7

An immunogenicity test was performed with the APMV1/Chicken/Mexico/RecP05/2005 strain of the Newcastle disease virus obtained according to Example 2, for which two different oil in water emulsion vaccine formulations were prepared at concentrations of 60/40 and 70/30.

Forty (40) 8-week old broilers were pooled in 4 groups and placed in Horsfall-Bauer type isolation units, identified with different color ring.

A group of chickens was vaccinated with a 0.5 ml dose of the emulsion vaccine at 60/40 concentration (Group A), the second group of chickens received a 0.5 ml dose of the emulsion vaccine at 70/30 concentration (Group B), the third group of chickens received the commercial vaccine Emulmax C IBH-ND (BG108).

TABLE 7.1

| Experimental design | | | |
|---|---|---|---|
| Group | Treatment received | No. Of birds | Dose (ml) |
| A | Emulsion vaccine 70/30 | 10 | 0.5 |
| B | Emulsion vaccine 60/40 | 10 | 0.5 |
| C | Control | 10 | NA |
| D | Vacuna comercial | 10 | 0.5 |

4 weeks after vaccination, each bird received 0.2 ml of APMV1/Chicken/Mexico/P05/2005 strain of the Newcastle disease virus, intramuscularly adjusted at a concentration of $10^6$ DIEP/ml.

The birds were bled every week to determine by HI antibodies for antigens LaSota, APMV1/Chicken/Mexico/P05/2005 and APMV1/Chicken/Mexico/RecP05/2005 strains of the Newcastle disease. The parameters to be evaluated were response to HI 4 weeks post-vaccination, protection against challenge and quantity of bioparticles in tracheal and cloacal swabs 3 and 7 days post-challenge.

TABLE 7.2

| Geometric mean (GM) of antibodies determination essays by HI of the LaSota strain of the Newcastle disease virus. | | | | | |
|---|---|---|---|---|---|
| Group | Bleeding 0 | Bleeding 1 | Bleeding 2 | Bleeding 3 | Bleeding 4 |
| A | 10 * | 10 | 21 | 139 | 113 |
| B | 10 | 10 | 16 | 46 | 46 |
| C | 10 | 10 | 10 | 10 | 10 |
| D | — | — | — | — | 226.3 |

* For the initial bleeding, only 10 animals were bled out of a total of 40.

TABLE 7.3

Geometric mean (GM) of antibodies determination essays by HI of the APMV1/Chicken/Mexico/P05/2005 strain of the Newcastle disease virus.

| Group | Bleeding 0 | Bleeding 1 | Bleeding 2 | Bleeding 3 | Bleeding 4 |
|---|---|---|---|---|---|
| A | 10 * | 10 | 65 | 33 | 57 |
| B | 10 | 10 | 33 | 20 | 21 |
| C | 10 | 10 | 10 | 10 | 10 |
| D | — | — | — | — | 61 |

* For the initial bleeding, only 10 animals were bled out of a total of 30.

TABLE 7.4

Geometric mean (MG) and Log 2 of antibodies determination essays by HI of the APMV1/Chicken/Mexico/RecP05/2005 strain of the Newcastle disease virus.

| | Bleeding 2 | | Bleeding 3 | | Bleeding 4 | |
|---|---|---|---|---|---|---|
| Group | mg | Log2 | mg | Log2 | mg | Log2 |
| A | 106 | 6.72 | 299 | 8.22 | 197 | 7.62 |
| B | 106 | 6.72 | 160 | 7.32 | 160 | 7.32 |
| C | 10 | 3.32 | 11 | 3.45 | 10 | 3.32 |

TABLE 7.5

Shows the mortality found after challenge with APMV1/Chicken/Mexico/P05/2005 strain.

| Group | No of birds | Mortality |
|---|---|---|
| A | 1 * | 10% |
| B | 1 | 10% |
| C | 10 ** | 100% |
| D | 0 | 0% |

* It was decided to cull the animal 12 days post-challenge, because it had shown signs during 9 days and its condition was worsening.
** The animals died between 3 and 4 days post-challenge.

TABLE 7.6

Shows individually the particle titers of Newcastle disease virus strain APMV1/Chicken/Mexico/P05/2005, detected through PCR rt test 3 days post-challenge (dpc) in tracheal swabs.

| Chicken No | A | B | D | C |
|---|---|---|---|---|
| 1 | $9.70 \times 10^5$ | $1.34 \times 10^4$ | $4.12 \times 10^4$ | $2.1 \times 10^7$ |
| 2 | $4.32 \times 10^5$ | Negativo | $1.558 \times 10^4$ | $1.252 \times 10^9$ |
| 3 | $5.34 \times 10^5$ | $2.72 \times 10^3$ | $3.08 \times 10^4$ | $6.38 \times 10^7$ |
| 4 | $1.75 \times 10^6$ | $3.36 \times 10^3$ | $8.58 \times 10^4$ | $1.12 \times 10^8$ |
| 5 | $5.54 \times 10^3$ | $2.62 \times 10^3$ | $6.22 \times 10^4$ | $1.172 \times 10^9$ |
| 6 | $3.18 \times 10^5$ | $3.08 \times 10^3$ | $3.14 \times 10^4$ | $2.32 \times 10^7$ |
| 7 | $1.94 \times 10^9$ | $4.4 \times 10^4$ | $4.86 \times 10^4$ | $4.56 \times 10^8$ |
| 8 | $5.58 \times 10^5$ | $3.44 \times 10^3$ | $2.28 \times 10^4$ | $1.49 \times 10^8$ |
| 9 | Negativo | $3.48 \times 10^3$ | $5.34 \times 10^4$ | $1.202 \times 10^9$ |
| 10 | Negativo | $2.8 \times 10^3$ | $5.38 \times 10^4$ | $6.54\ 10^6$ |
| mg | $10^{4.78}$ | $10^{3.68}$ | $10^{4.60}$ | $10^{8.14}$ |
| Diferencia | 3.36 | 4.46 | 3.54 | 0.0 |

TABLE 7.7

Shows individually the viral particles titers of APMV1/Chicken/Mexico/P05/2005 strain of the Newcastle disease virus, detected by rt-PCR 3 days post-challenge (dpc) in cloacal swabs.

| Chicken No | A | B | D | C |
|---|---|---|---|---|
| 1 | $3.40 \times 10^5$ | $1.416 \times 10^4$ | NP | $1.906 \times 10^7$ |
| 2 | $8.26 \times 10^5$ | $8.66 \times 10^3$ | NP | $1.938 \times 10^8$ |
| 3 | $8.2 \times 10^5$ | $2.86 \times 10^3$ | NP | $6.10 \times 10^5$ |
| 4 | $2.74 \times 10^5$ | $4.2 \times 10^3$ | NP | $4.96 \times 10^6$ |
| 5 | $4.76 \times 10^5$ | $1.69 \times 10^3$ | $5.02 \times 10^4$ | $2.58 \times 10^6$ |
| 6 | $1.094 \times 10^6$ | $9.66 \times 10^2$ | $3.18 \times 10^4$ | $1.076 \times 10^8$ |
| 7 | $2.58 \times 10^5$ | $3.76 \times 10^3$ | $1.478 \times 10^6$ | $1.24 \times 10^7$ |
| 8 | $1.688 \times 10^5$ | $2.1 \times 10^3$ | $5.8 \times 10^6$ | $1.308 \times 10^6$ |
| 9 | $5.36 \times 10^5$ | $3.38 \times 10^3$ | $1.49 \times 10^6$ | $3.06 \times 10^7$ |
| 10 | $3.88 \times 10^5$ | $1.842 \times 10^3$ | $8.02 \times 10^5$ | $6.5 \times 10^6$ |
| MG | $10^{5.65}$ | $10^{3.5}$ | $10^{5.7}$ | $10^{7.0}$ |
| Difference | 1.35 | 3.5 | 1.3 | 0.0 |

NP = Not performed because of lack of samples.

TABLE 7.8

Shows individually the viral particles titers of the APMV1/Chicken/Mexico/P05/2005 strain of the Newcastle disease virus, detected by rt-PCR 7 days post-challenge (dpc) on tracheal swabs

| Chicken No. | A | B | D | C |
|---|---|---|---|---|
| 1 | $1.036 \times 10^6$ | $2.6 \times 10^4$ | $8.3 \times 10^5$ | ND |
| 2 | $6.14 \times 10^5$ | $5.76 \times 10^3$ | $2.76 \times 10^6$ | ND |
| 3 | $6.38 \times 10^5$ | $2.38 \times 10^3$ | $1.982 \times 10^6$ | ND |
| 4 | Negative | $5.22 \times 10^3$ | $9.6 \times 10^6$ | ND |
| 5 | $8.72 \times 10^5$ | $3.44 \times 10^3$ | $3.1 \times 10^6$ | ND |
| 6 | $1.342 \times 10^6$ | $6.44 \times 10^4$ | $1.428 \times 10^6$ | ND |
| 7 | Negative | $1.94 \times 10^5$ | $7.46 \times 10^7$ | ND |
| 8 | $5.76 \times 10^5$ | $3.76 \times 10^4$ | $4.34 \times 10^6$ | ND |
| 9 | $6.06 \times 10^5$ | $9.66 \times 10^4$ | $1.518 \times 10^6$ | ND |
| 10 | $6.44 \times 10^5$ | $5.5 \times 10^4$ | $2.96 \times 10^6$ | ND |
| MG | $10^{4.70}$ | $10^{4.3}$ | $10^{6.5}$ | |

ND = Not determined because the birds died within 3 and 5 days post-challenge.

TABLE 7.9

Shows individually the viral particle titers of the APMV1/Chicken/Mexico/P05/2005 strain of the Newcastle disease virus detected by rt-PCR 7 days post-challenge (dpc) on tracheal swabs.

| Chicken No. | A | B | D | C |
|---|---|---|---|---|
| 1 | Negative | $3.88 \times 10^3$ | $8.9 \times 10^5$ | ND |
| 2 | $1.61 \times 10^5$ | $4.18 \times 10^3$ | $5.86 \times 10^5$ | ND |
| 3 | $2.04 \times 10^6$ | $3.24 \times 10^4$ | $4.6 \times 10^6$ | ND |
| 4 | $5.48 \times 10^5$ | $2.36 \times 10^4$ | $1.854 \times 10^6$ | ND |
| 5 | Negative | $5.66 \times 10^4$ | $1.304 \times 10^6$ | ND |
| 6 | $6.92 \times 10^5$ | $8.04 \times 10^4$ | $5.60 \times 10^5$ | ND |
| 7 | $2.94 \times 10^6$ | $1.2 \times 10^4$ | $1.056 \times 10^6$ | ND |
| 8 | $9.04 \times 10^5$ | $2.68 \times 10^4$ | $6.06 \times 10^6$ | ND |
| 9 | $1.258 \times 10^3$ | $6.16 \times 10^4$ | $1.124 \times 10^6$ | ND |
| 10 | $8.24 \times 10^3$ | $1.35 \times 10^4$ | $1.646 \times 10^6$ | ND |
| MG | $10^{4.2}$ | $10^{4.3}$ | $10^{6.16}$ | |

ND = Not determined because the birds died within 3 and 5 days post-challenge.

HI results show that chickens vaccinated with APMV1/Chicken/Mexico/RecP05/2005 virus have a greater response with the recombinant homologous antigen and a poor response towards the LaSota strain of the Newcastle disease antigen (113) compared to the vaccine prepared with LaSola antigen which had a geometric mean of 226.3. There was no difference in protection against challenge since the 3 groups evaluated were satisfactory.

With regard to viral recovery on tracheal swabs 3 days post-challenge, there was a difference greater than log 3 lower in the 3 vaccinated groups, being group B (Vaccinated with the APMV1/Chicken/Mexico/RecP05/2005 virus of the present invention) the group showing the lowest virus recovery. Likewise, group B vaccinated with an oil in water emulsion (60/40) showed the lowest viral shedding in cloacal swabs 3 days post-challenge. The conclusion of the instant work is that the APMV1/Chicken/Mexico/RecP05/2005 strain is immunogenic, granting 100% protection against a pathogen strain of the Newcastle disease virus and reducing viral shedding in vaccinated birds.

REFERENCES

Mayo, M. A. (2002). Virus taxonomy—Houston 2002. Arch. Virol. 147: 1071-1076.

Glickman, R. L., Syddall, R. J., Iorio, R. M., Sheehan, J. P., Bratt, M. A., 1988. Quantitative basic residue requirements in the cleavage-activation site of the fusion glycoprotein as a determinant of virulence for Newcastle disease virus. J. Virol. 62, 354-356.

Peeters, B. P., de Leeuw, O. S., Koch, G. & Gielkens, A. L. (1999). Rescue of Newcastle disease virus from cloned cDNA: evidence that cleavability of the fusion protein is a major determinant for virulence. J Virol 73, 5001-5009.

de Leeuw, O. S. and B. Peeters, 1999. Complete nucleotide sequence of Newcastle disease virus: evidence for the existence of a new genus within the subfamily Paramyxovirinae. J. Gen. Virol., 80: 131-136.

Cobaleda, C., Muñoz-Barroso, I., Sagrera, A. and Villar, E. (2002) Fusogenic activity of reconstituted Newcastle disease virus envelopes: a role for the hemagglutinin-neuraminidase protein in the fusion process. Int. J. Biochem. Cell Biol 34 pp 403-413.

Czeglédi, A., Ujvári, D., Somogyi, E., Wehmann, E., Werner, O., Lomniczi, B., 2006. Third genome size category of avian paramyxovirus serotype 1 (Newcastle disease virus) and evolutionary implications. Virus Research 120, 36-48.

Fuerst, T. R., Earl, P. L. & Moss, B. (1987). Use of a hybrid vaccinia virus-T7 RNA polymerase system for expression of target genes. Molecular and Cellular Biology 7, 2538-2544.

Alexander D. Newcastle disease, Other Avian Paramyxoviruses, and Pneumovirus Infections. En Disease of Poultry 11ª edición. Editado por H. J. Barnes; A. M. Fadly; J. R. Glisson; L. R. McDougald; y D. E. Swayne.

Seal B. S., King D. J. y Bennett J. D. (1995) Characterization of Newcastle disease Virus Isolates by Reverse Transcription PCR Coupled to Direct Nucleotide Sequencing and Development of Sequence Database for Pathotype Prediction and Molecular Epidemiological Analysis. J. Clin. Microbiol. 33(10): 2624-2630.

Having described the invention, it is considered a novelty and we therefore claim as our property the contents of the following clauses:

1. A recombinant Newcastle disease virus containing nucleotide sequences encoding NP, P, M, L, F and HN proteins, wherein the nucleotide sequence encoding the F and HN proteins comprises the nucleotide sequence of SEQ ID NO: 1.

2. The recombinant Newcastle disease virus of claim 1, wherein said virus has the nucleotide sequence of SEQ ID NO: 2.

3. The recombinant Newcastle disease virus of claim 1, wherein said virus has the nucleotide sequence of SEQ ID NO: 3.

4. The recombinant Newcastle disease virus of claim 1, wherein said virus has the nucleotide sequence of SEQ ID NO: 4.

5. The recombinant Newcastle disease virus of claim 1 wherein said virus has the nucleotide sequence of SEQ ID NO: 5.

6. A vaccine for protecting a bird against Newcastle disease and for reducing viral shedding, comprising the recombinant Newcastle disease virus of claim 1, wherein the recombinant Newcastle disease virus is homologous to a challenge virus.

7. A vaccine for protecting a bird against Newcastle disease and for reducing viral shedding, comprising the recombinant Newcastle disease virus of claim 2, wherein the recombinant Newcastle disease virus is homologous to a challenge virus.

8. A vaccine for protecting a bird against Newcastle disease and for reducing viral shedding, comprising the recombinant Newcastle disease virus of claim 3, wherein the recombinant Newcastle disease virus is homologous to a challenge virus.

9. A vaccine for protecting a bird against Newcastle disease and for reducing viral shedding, comprising the Newcastle disease virus of claim 4, wherein the recombinant Newcastle disease virus is homologous to a challenge virus.

10. A vaccine for protecting a bird against Newcastle disease and for reducing viral shedding comprising the recombinant Newcastle disease virus of claim 5, wherein the recombinant Newcastle disease virus is homologous to a challenge virus.

11. A vector comprising the nucleotide sequence of SEQ ID No 1.

12. A method for protecting against Newcastle disease in a bird, comprising administering to the bird the vaccine of claim 6.

13. A method for protecting against Newcastle disease in a bird, comprising administering to the bird the vaccine of claim 7.

14. A method for protecting against Newcastle disease in a bird, comprising administering to the bird the vaccine of claim 8.

15. A method for protecting against Newcastle disease in a bird, comprising administering to the bird the vaccine of claim 9.

16. A method for protecting against Newcastle disease in a bird, comprising administering to the bird the vaccine of claim 10.

17. An isolated nucleic acid molecule comprising the nucleotide sequence of SEQ ID NO: 1.

18. A vaccine for protecting a bird against Newcastle disease and for reducing viral shedding comprising the isolated nucleic acid molecule of claim 17, wherein SEQ ID NO: 1 encodes F and HN proteins that are homologous to F and HN proteins, respectively, of a challenge virus.

19. A method for protecting against Newcastle disease in a bird, comprising administering to the bird the vaccine of claim 18.

* * * * *